(12) United States Patent
Gonsalves et al.

(10) Patent No.: US 6,818,804 B1
(45) Date of Patent: *Nov. 16, 2004

(54) TOSPOVIRUS RESISTANCE IN PLANTS

(75) Inventors: Dennis Gonsalves, Geneva, NY (US); Sheng-Zhi Pang, Chesterfield, MO (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/426,783

(22) Filed: Oct. 22, 1999

Related U.S. Application Data

(63) Continuation of application No. 08/495,484, filed as application No. PCT/US94/01046 on Jan. 27, 1994, now Pat. No. 6,329,568.

(51) Int. Cl.$^7$ .......................... C12N 15/90; C12N 15/82; A01H 5/00
(52) U.S. Cl. .................... 800/280; 435/320.1; 435/419; 435/468; 800/285
(58) Field of Search ............................. 435/320.1, 410, 435/418, 419, 468; 536/23.72; 800/278, 280, 295, 298, 301, 279

(56) References Cited

U.S. PATENT DOCUMENTS

| 5,583,021 A | 12/1996 | Dougherty et al. ......... 800/280 |
| 5,939,600 A | 8/1999 | Goldbach et al. ........... 800/280 |

FOREIGN PATENT DOCUMENTS

| AU | A-32166/93 | 12/1993 | |
| EP | 426195 | 5/1991 | |
| EP | 0 558 944 A2 | 9/1993 | ........... C12N/15/11 |
| EP | 0 566 525 A2 | 10/1993 | ........... C12N/15/40 |

OTHER PUBLICATIONS

Peters et al., "The Biology of Tospovirues" In Pathogenesis and Host Specificity in Plant Diseases, vol. III, Viruses and Viroids. R.P. Singh, U.S. Singh, and K. Kohmoto, Eds., Pergamon Press, 1995.*
Lindbo et al., "Pathogen–Derived REsistance to a Potyvirus: Immune and Resistant Phenotypes in Transgenic Tobacco Expression Altered Forms of a Potyvirus Coat Protein Nucleotide Sequence," *Molecular Plant–Microbe Interactions* 5(2):144–153 (1992).
Pang et al., "Different Mechanisms Protect Transgenic Tobacco Against Tomato Spotted Wilt and Impatients Necrotic Spot *Tospoviruses,*" *Bio/Technology* 11:819–824 (1993).
Lindbo et al., "Untranslatable Transcripts of the Tobacco Etch Virus Coat Protein Gene Sequence Can Interfere with Tobacco Etch Virus Replication in Transgenic Plants and Protoplasts," *Virology* 189:725–733 (1992).

Bejarano et al., "Prospects for Engineering Virus Resistance in Plants with Antisense RNA," *Tibtech* 10:383–388 (1992).
Wang, M., et al., "ELISA Detection of Various Tomato Spotted Wilt Virus Isolates Using Specific Antisera to Structural Proteins of the Virus," *Plant Disease* 74(2):154–58 (1990).
Vaira, A.M., et al., "Resistance to Tospoviruses in *Nicotiana benthamiana* Transformed with the N Gene of Tomato Spotted Wilt Virus Correlation Between Transgene Expression and Protection in Primary Transformants," *MPMI* 8(1):66–73 (1995).
Prins, M. et al., "Broad Resistance to Tospovirus in Transgenic Tobacco Plants Expressing Three Tospoviral Nucleoprotein Gene Sequences," *MPMI* 8(1):85–91 (1995).
Pang, S., et al., "The Biological Properties of a Distinct Tospovirus and Sequence Analysis of Its S RNA," *Phytopathology* 83(7):728–733 (1993).
de Haan, P., et al., "Characterization of RNA–Mediated Resistance to Tomato Spotted Wilt Virus in Transgenic Tobacco Plants," *Biotechnology* 10:1133–37 (1992).
Pang, S., et al., "Use of the Signal Peptide of PISUM Vicilin to Translocate Beta–glucuronidase in *Nicotiana tabacum*" *Gene* 112:229–234 (1992).
Law, M.D., et al., "A Tomato Spotted Wilt–like Virus With a Serologically Distinct N Protein," *J. gen. Virol.* 71:933–938 (1990).
De Haan, P., et al., "Tomato Spotted Wilt Virus L RNA Encodes a Putative RNA Polymerase," *J. gen. Virol.* 71:2207–2216 (1991).
Maiss, E., et al., *J. gen. Virol.* "Cloning and sequencing of the S RNA from a Bulgarian isolate of Tomato Spotted Wilt Virus," *Journal of General Virology* 72:461–464 (1991).
MacKenzie, D.J., et al., "Resistance to Tomato Spotted Wilt Virus Infection in Transgenic Tobacco Expressing the Viral Nucleocapsid Gene," *Molecular Plant–Microbe Interactions* 5:34–40 (1992).
Morelle, G., "A Plasmid Extraction Procedure on a Miniprep Scale," *Focus* 11:7 (1989).
Mohamed, N.A., et al., "Protein Composition of Tomato Spotted Wilt Virus," *Virology* 56:12–21 (1973).

(List continued on next page.)

Primary Examiner—Ashwin Mehta
(74) Attorney, Agent, or Firm—Nixon Peabody LLP

(57) ABSTRACT

The nucleotide sequences for tomato spotted wilt virus (TSWV) nucleocapsid is described, and transgenic plants containing the nucleocapsid nucleotide sequence from a TSMV isolate is shown to provide resistance in the transgenic plant to *Tospoviruses* from different serogrotips. In addition, transgenic plants containing the nucleocapsid nucleotide sequence from a lettuce isolate of TSWV were produced and shown to provide (in plants producing small amounts of the nucleocapsid protein) resistance in the transgenic plant to both homologous and closely related viral isolates whereas plants producing larger amounts of the nucleocapsid protein possessed moderate levels of protection against both the homologous isolate and isolates of distantly related Impatiens necrotic spot virus (INSV).

7 Claims, 5 Drawing Sheets

OTHER PUBLICATIONS

Urban, L.A., et al., "Cytoplasmic Inclusions in Cells Infected with Isolates of L and I Serogroups of Tomato Spotted Wilt Virus," *The American Phytopathological Society* 81(5):525–529 (1991).

Cho, J.J., et al., "A Multidisciplinary Approach to Management of Tomato Spotted Wilt Virus in Hawaii," *Plant Disease* 73(5):375–383 (1989).

Iwaki, M., et al., "Silver Mottle Disease of Watermelon Caused by Tomato Spotted Wilt Virus," *Plant Disease* 68:1006–1008 (1984).

Gonsalves, D., et al., "Tomato Spotted Wilt Virus in Papaya and Detection of the Virus by ELISA," *Plant Disease* 70:501–506 (1986).

Siemieniak, D.R., et al., "Strategy and Methods for Directly Sequencing Cosmid Clones," *Analytical Biochemistry* 192:441–448 (1991).

Horsch, R.B., et al., "A Simple and General Method for Transferring Genes Into Plants," *Science* 27:1229–1231 (1985).

Van Den Hurk, J., et al., "The Ribonucleic Acid of Tomato Spotted Wilt Virus," *J. gen. Virol.* 36:81–91 (1977).

Tas, P.W.L., et al., "The Structural Proteins of Tomato Spotted Wilt Virus," *J. gen. Virol.* 36:267–279 (1977).

Mohamed, N.A., "Isolation and Characterization of Subviral Structures From Tomato Spotted Wilt Virus," *J. gen. Virol.* 53:197–206 (1981).

Pang, S.Z., et al., "Resistance to Heterologous Isolates of Tomato Spotted Wilt Virus in Transgenic Tobacco Expressing its Nucleocapsid Protein Gene," *Molecular Plant Pathology* 82(10):1223–1229 (1992).

MacKenzie, D.J., "Resistance to Tomato Spotted Wilt Virus Infection in Transgenic Tobacco Expression the Viral Nucleocapsid Gene," *Molecular Plant–Microbe Interactions*, 5(1):34–40 (1992).

Kim, J.W., et al., "Disease Resistance in Tobacco and Tomato Plants Transformed with the Tomato Spotted Wilt Virus Nucleocapsid," *Plant Disease* 78(6):615–621 (1994).

Kurppa, A., et al., "Use of Double Stranded RNA for Detection and Identification of Virus Diseases of Rubus Species," *Acta Horticulturae* 186:56–62 (1986).

Pang, S.Z., et al., "Resistance of Transgenic *Nicrotiana benthamiana* Plants to Tomato Spotted Wilt and Impatients Necrotic Spot Tospoviruses: Evidence of Involvement of the N Protein and N Gene RNA in Resistance," *Phytophatology* 84(3):243–249 (1994).

T.L. German, et al., "*Tospoviruses*: Diagnosis, Molecular Biology, Phsylogeny, and Vector Relationships," *Annu. Rev. Phytopathol* 30:315–348 (1992).

Gubler, U., et al., "A Simple and Very Efficient Method for Generating cDNA Libraries," *Gene* 25:263–269 (1983).

Holsters, M., et al., "Transfection and Transformation of *Agrobacterium tumefaciences*," *Molec. gen. Genet.* 163:181–187 (1978).

Kim, J.W., Sequence Accession No: X61799 (1991).

De Haan, P., et al., "Molecular Cloning and Terminal Sequence Determination of the S and M RNAs of Tomato Spotted Wilt Virus," *J. gen. Virol.* 70:3469–73 (1989).

Gielen, J.J.L., et al., "Engineered Resistance to Tomato Spotted Wilt Virus, A Negative–Strand RNA Virus," *Biotechnology* 9:1363–67 (1991).

Nejidat, A., et al., "Engineered Resistance Against Plant Virus Disease," *Physiologia Plantarum* 80:662–68 (1990).

Kawchuk, L.M., et al., "Sense and Antisense RNA–Mediated Resistance to Potato Leafroll Virus in Russet Burbank Potato Plants," *Molecular Plant–Microbe Interactions* 4(3):247–53 (1991).

\* cited by examiner

TOSPOVIRUS RESISTANCE IN PLANTS

This application is a continuation of U.S. patent application Ser. No. 08/495,484, now U.S. Pat. No. 6,329,568, filed Sep. 25, 1995, as a national stage application of PCT Application No. PCT/US94/01046 filed Jan. 27, 1994, which claims the priority benefit of U.S. patent application Ser. No. 08/010,410 filed Jan. 29, 1993, now abandoned.

Viruses in the *Tospovirus* genus infect a wide variety of plant species, particularly tobacco, peanut, vegetables and ornamental plants. Two virus species, tomato spotted wilt virus (TSWV) and impatiens hecrotic spot virus (INSV) are recognized within the *Tospovirus* genus.

Tomato Spotted Wilt Virus (TSWV) is unique among plant viruses in that the nucleic acid-protein complex is covered by a lipoprotein envelope and it is the only thrip transmitted virus. This virus has recently been classified as the *Tospovirus* genus of the Bunyaviridae family. TSWV virions contain a 29K nucleocapsid protein ("NP" or "N"), two membrane-associated glycoproteins (58K and 78K) and a large 200K protein presumably for the viral transcriptase [see J. Gen. Virol. 71:2207 (1991); Virol. 56:12 (1973); and J. Gen. Virol. 36:267 (1977)]. The virus genome consists of three negative-strand (−) RNAs designated L RNA (8900 nucleotides), M RNA (5400 nucleotides) and S RNA (2900 nucleotides) [see J. Gen. Virol. 36:81 (1977); J. Gen. Virol. 53:12 (1981); and J. Gen. Virol. 70:3469 (1989)], each of which is encapsulated by the NP. The partial or full-length sequences of S RNAs from three TSWV isolates reveals the presence of two open reading frames (ORF) with an ambisense gene arrangement [see J. Gen Virol. 71:1 (1990) and J. Gen. Virol. 72:461 (1991)]. The larger open reading frame is located on the viral RNA strand and has the capacity to encode a 52K nonstructural protein. The smaller ORF is located on the viral complementary RNA strand and is translated through a subgenomic RNA into the 29K NP.

The ambisense coding strategy is also characteristic of the TSWV M RNA, with the open reading frames encoding the 58K and 78K membrane-associated glycoproteins. The TSWV L RNA has been sequenced to encode a large 200K protein presumably for the viral transcriptase.

Two TSWV serogroups, "L" and "I", have been identified and characterized based on serological analysis of the structural proteins and morphology of cytopathic structures [see J. Gen Virol. 71:933 (1990) and Phytopathology 81:525 (1991)]. They have serologically conserved G1 and G2 glycoproteins, but the NP of the "I" serogroup is serologically distinct from that of the "L" serogroup. Comparison of the NP between the "L" and "I" serogroups has shown 62% and 67% identifies at nucleotide and amino acid levels, respectively [see J. Gen. Virol. 72:2597 (1991)].

TSWV has a wide host range, infecting more than 360 plant species of 50 families and causes significant economic losses to vegetables and ornamental plants worldwide. The "L" serogroup has been found extensively in field crops such as vegetables and weeds, while the "I" serogroup has been largely confined to ornamental crops. A cucurbit isolate has recently been identified [see Plant Disease 68:1006 (1984)] as a distinct isolate because it systemically infects watermelon and other curcurbits and its NP is serologically unrelated to that of either serogroup. Although the spread of the TSWV disease can sometimes be reduced by breeding resistant plants or using non-genetic approaches, complete control of the disease by these conventional methods has generally proven to be difficult [see Plant Disease 73:375 (1989)].

Since 1986, numerous reports have shown that transgenic plants with the coat protein (CP) gene of a virus are often resistant to infection by that virus. This phenomenon is commonly referred to as coat protein-mediated protection (CPMP). The degree of protection ranges from delay in symptom expression to the absence of disease symptoms and virus accumulation. Two recent independent reports [see Biol. Technology 9:1363(1991) and Mol. Plant-Microbe Interact. 5:34 (1992)] showed that transgenic tobacco plants expressing the nucleocapsid protein (NP) gene of TSWV are resistant to infection by the homologous isolate. However, since TSWV is widespread with many biologically diverse isolates, it is very important to test the effectiveness of the transgenic plants to resist infections by different TSWV isolates. The findings of the present invention expand on those of the previous reports by demonstrating that transgenic plants according to the present invention showed resistance to two heterologous isolates of the "L" serogroup and an isolate of the "I" serogroup. We also show that resistance to the two heterologous isolates of the "L" serogroup was mainly found in plants accumulating very low, if any, levels of NP, while transgenic plants that accumulated high levels of NP were resistant to the isolate of the "I" serogroup.

However, no resistance was observed to a Brazillian isolate, although the plants that accumulated high levels of the N protein did display a delay in symptom expression. This Brazillian isolate, designated TSWV-B has the N protein that was serologically distinct from the "L" and "I" serogroups and biologically differs from a curcurbit isolate in that the TSWV-B does not systemically infect melons or squash. Therefore, one aspect of the present invention is to characterize the TSWV-B by cloning and sequencing of its S RNA and comparisons with the published sequences of other TSWV isolates.

Various aspects of the present invention will become readily apparent from the detailed description of the present invention including the following example, figures and data.

In the figures;

FIG. 3 depicts the location of the sequenced cDNA clones in the TSWV-B S RNA according to the present invention;

FIG. 4 depicts a dendogram showing relationships among TSWV isolates according to the present invention;

Figure 7:
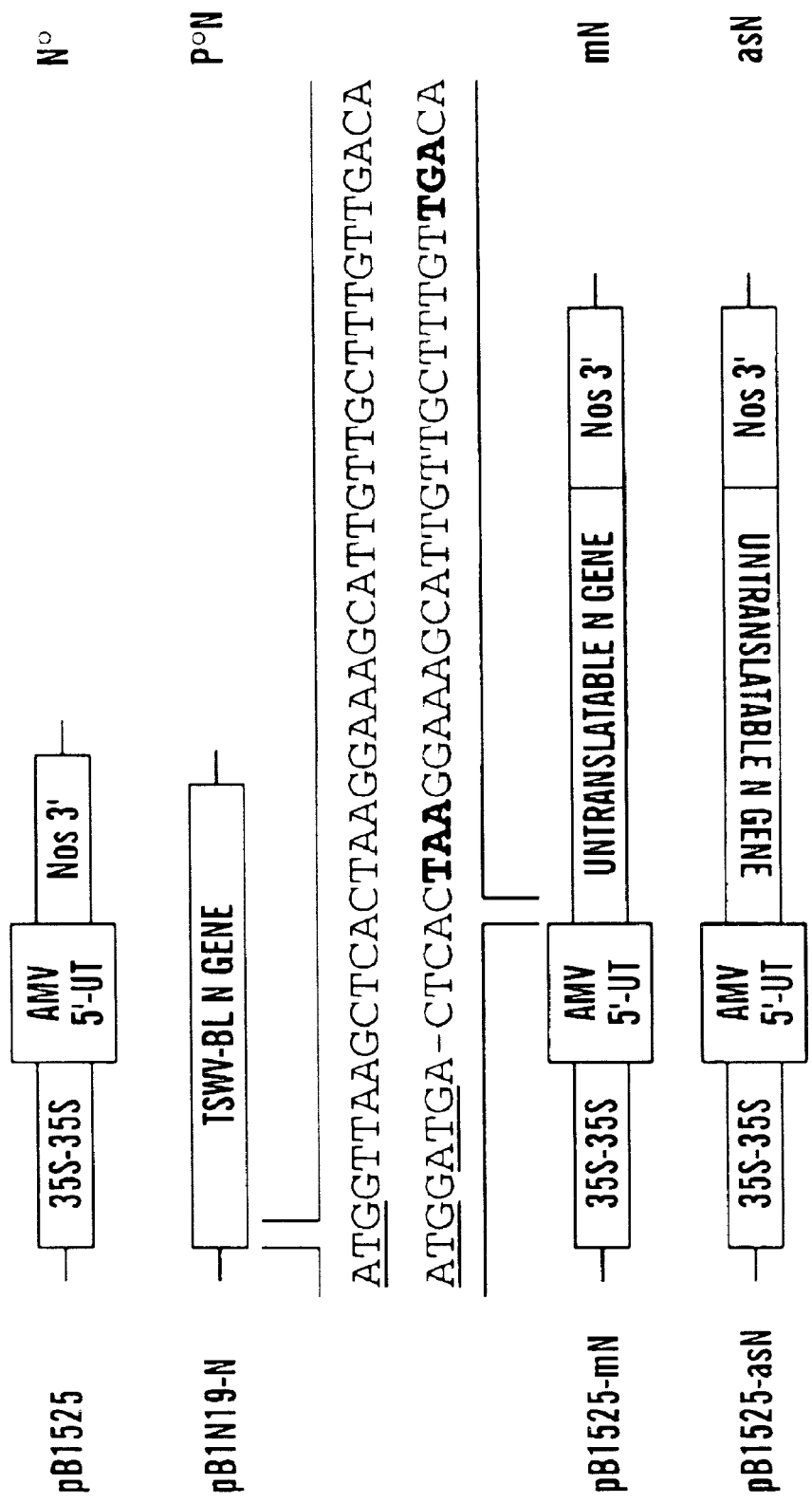
Figure 8:
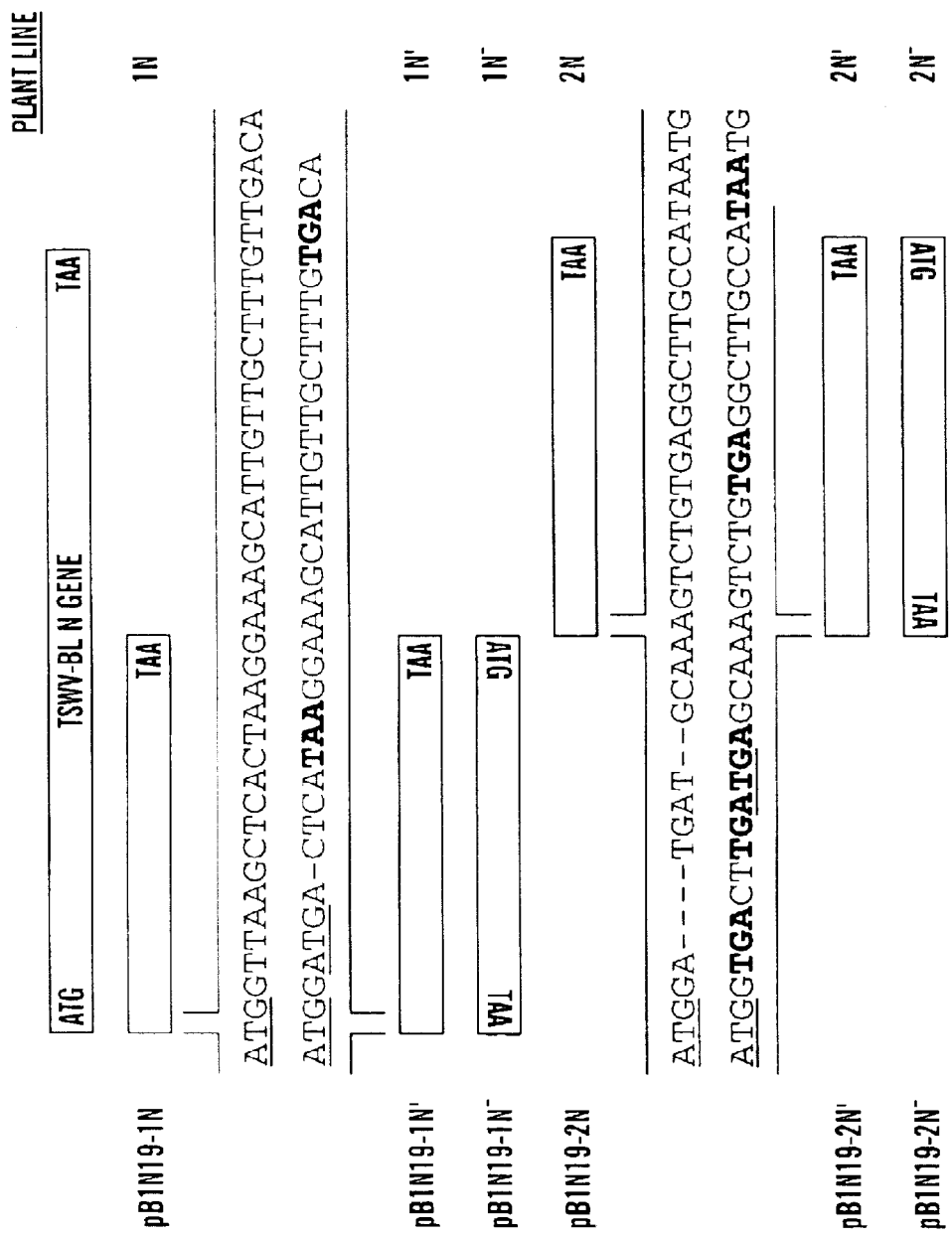

FIG. 7 depicts the TSWV-BL N coding sequences introduced into transgenic plants in accordance with one aspect of the present invention, with the 5' terminal DNA sequences shown for the TSWV-BL N gene in the pBIN19-N construct (SEQ. ID. No.: 31) and for the mutated, untranslatable N gene in the pB1525-mN construct (SEQ. ID. No.: 32) and FIG. 8 depicts the TSWV-BL half N gene fragments introduced into plants in accordance with one aspect of the present invention, with the 5' terminal DNA sequences shown for the TSWV-BL half N gene in the pBIN19-1N construct (SEQ. ID. No.: 31), the mutated, untranslatable half N gene in the pBIN19-1N' construct (SEQ. ID. No. 33), the half N gene in the pBIN19-2N construct (SEQ. ID. No.: 34), and the mutated, untranslatable half N gene in the pBIN19-2N' construct (SEQ. ID. No.: 35).

Figure 1:
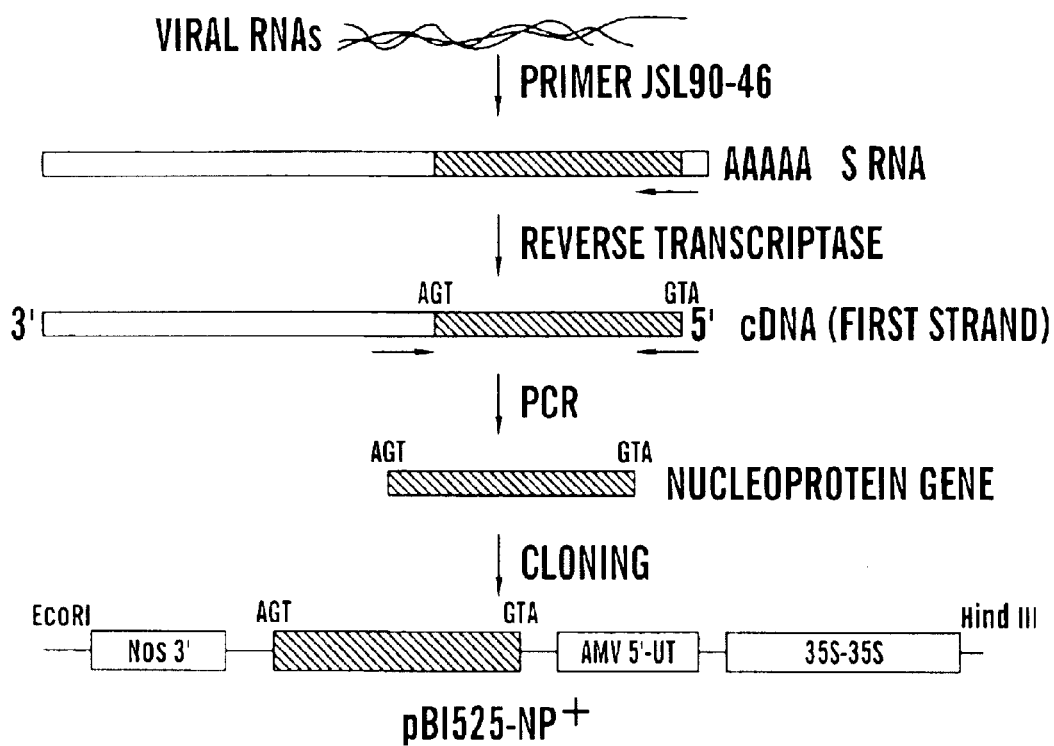
FIG. 1 depicts the strategy for cloning the NP gene from viral RNA according to the present invention.
Figure 2:
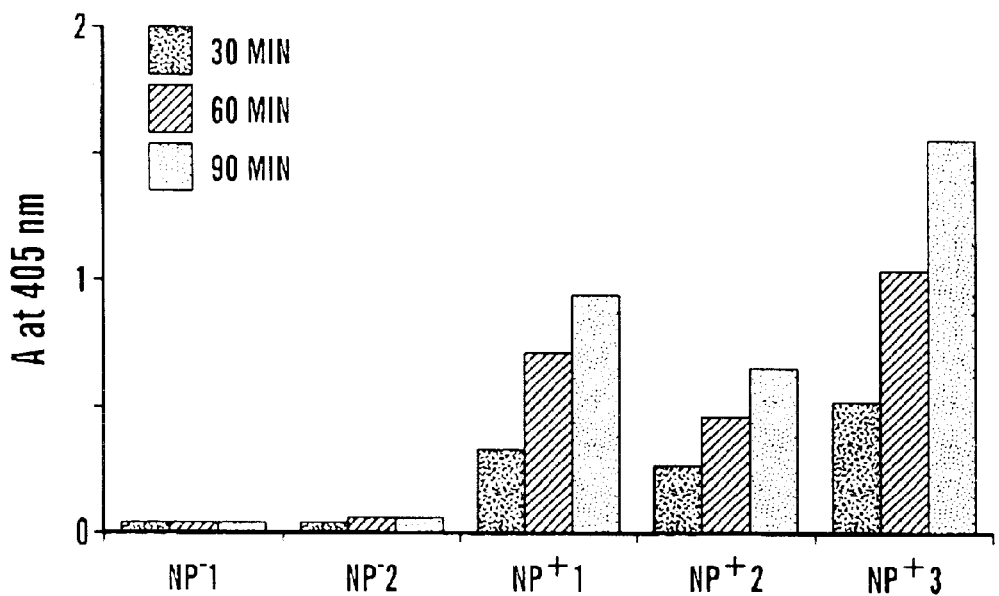
FIG. 2 depicts the in vivo transient expression of the nucleocapsid protein (NP) gene of tomato spotted wilt virus according to the present invention in tobacco protoplasts.

More specifically, FIG. 2 depicts transient expression of the NP gene in which the constructs were transferred into tobacco mesophyll protoplasts using polyethylene glycol (PEG). The transformed protoplasts were subsequently incubated for two days for the expression of the NP gene. Proteins were extracted from the protoplasts and tested for the NP by double antibody sandwich enzyme-linked immunosorbent assay (DAS-ELISA) using antibodies against the TSWV NP, NP⁻ and NP⁺ represent the protoplasts transformed with plasmids pB1525-NP⁻ and pB1525-NP⁺, respectively. Concentration of the antibodies for coating: 5 µg/ml: dilution of the enzyme conjugate: 1:250. Data were taken 30, 60 and 90 min. after addition of substrate.

Figures 3, 4:
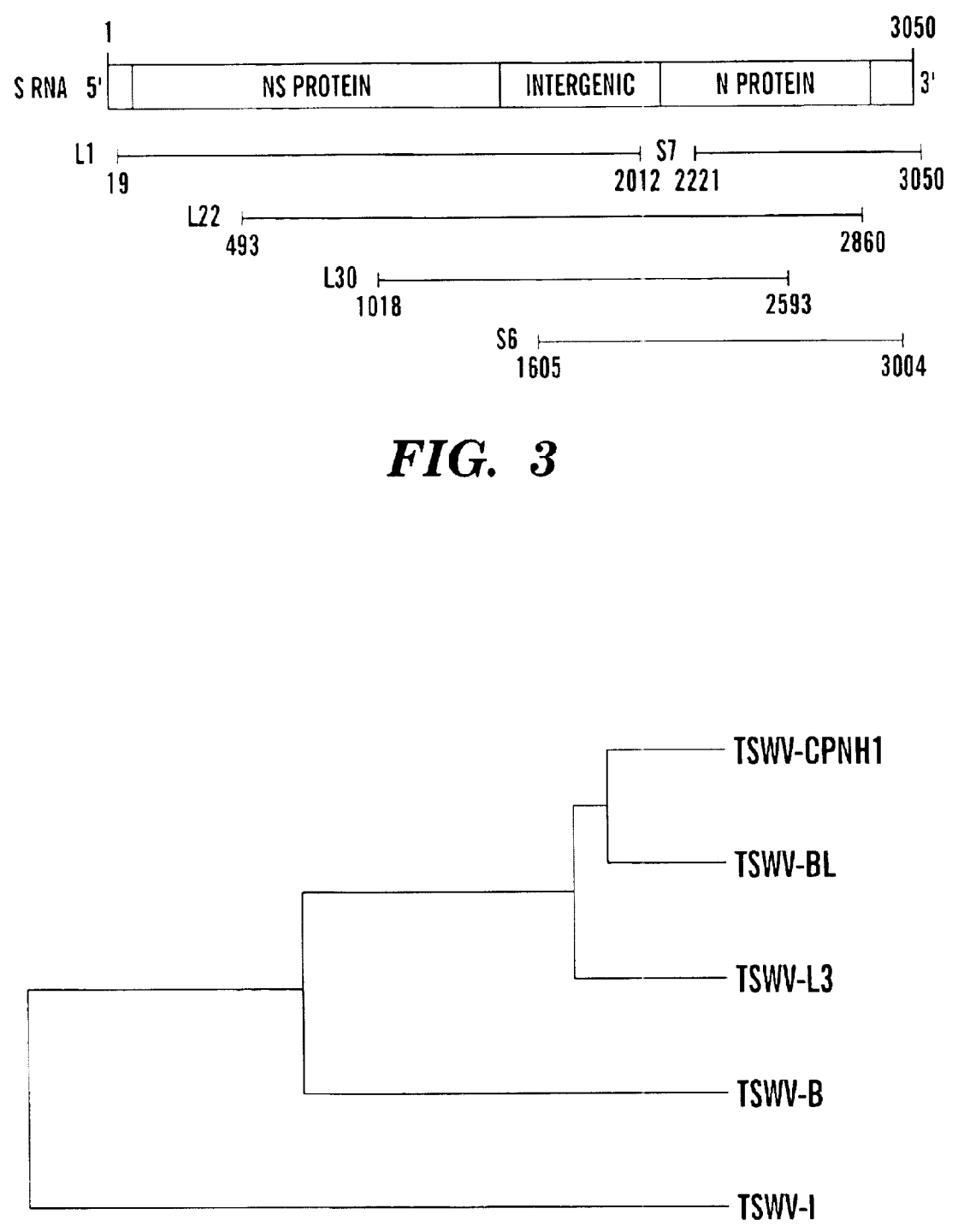

In FIG. 3, the five overlapping cDNA clones are shown to scale below a S RNA map of TSWV-B. These clones were synthesized with random primers from double-stranded RNA isolated from *N. benthamiana* plants infected with TSWV-B.

In FIG. 4, the sequences were compared using the pileup program of the GCG Sequence analysis software package. Horizontal lines are proportional to the genetic distance while vertical lines are of arbitrary length and have no significance.

Figure 5:
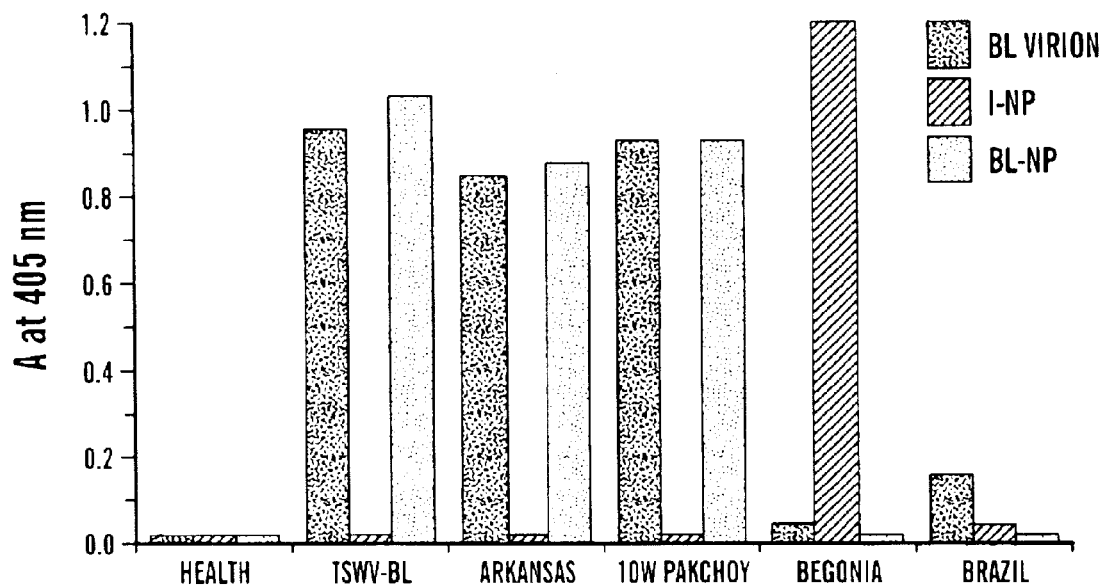
FIG. 5 depicts the serological relationship of TSWV isolates described herein.

More specifically, in FIG. 5, *N. benthamiana* Domin. were infected with TSWV isolates [TSWV-BL (a lettuce isolate), Arkansas, 10W pakchoy (TSWV-10W), Begonia, and Brazil (TSWV-B)). An infected leaf disc (0.05 gram) was ground in 12 ml of the enzyme conjugate buffer and analyzed by DAS-ELISA using antibodies raised against TSWV-BL virion (BL virion), or the NP of TSWV-BL (BL-NP), or TSWV-I (I-NP). Concentration of antibodies for coating were 1 µg/ml; dilution of conjugates were 1:2000 for BL virion, 1:250 for BL-NP, and 1:1000 for I-NP. The results were taken after 10 minutes (BL), 50 minutes (BL-NP), or 30 minutes after adding substrate.

Figure 6:
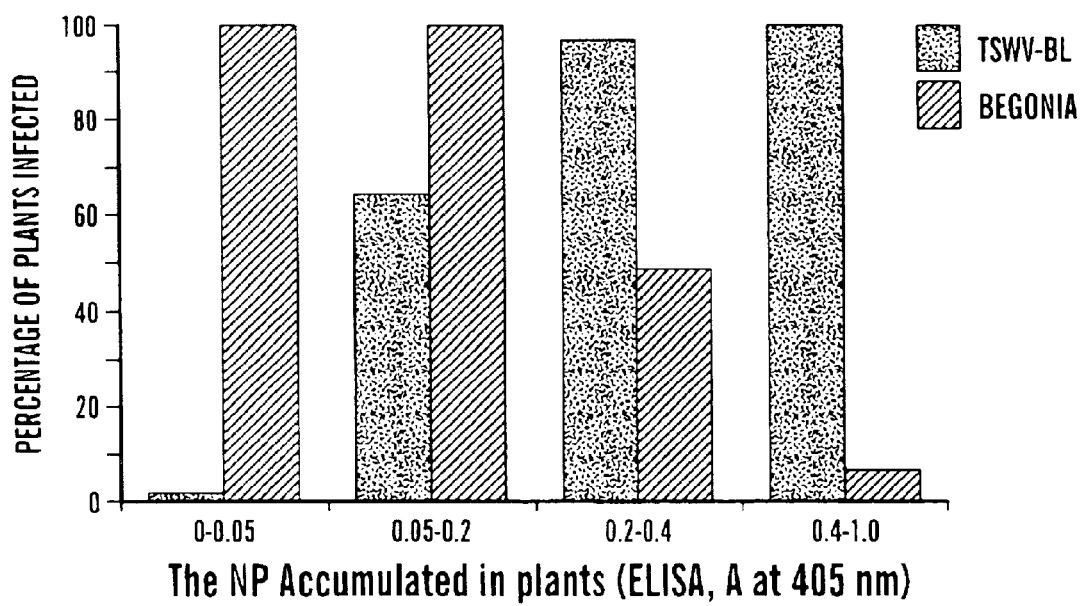
FIG. 6 depicts the correlation of the level of nucleocapsid protein (NP) accumulation in transgenic plants with the degree of resistance to TSWV isolates.

With regard to FIG. 6, transgenic plants were assayed in DAS-ELISA for NP accumulation with antibodies raised against the NP of TSWV-BL. Plants were read 150 min. after adding substrate and the transgenic plants were grouped into four categories: $OD_{405\ nm}$ smaller than 0.050, $OD_{405\ nm}$ between 0.050 to 0.200, $OD_{405\ nm}$ between 0.200 to 0.400, and $OD_{405\ nm}$ greater than 0.400. The $OD_{405\ nm}$ readings of control NP (−) plants were from zero to 0.05. The same plants were challenged with either the Arkansas (Ark) and 10W pakchoy (10W) isolates or the Begonia isolate and the susceptibility of each plant was recorded about 12 days after inoculation. The results were pooled from fifty-one $R_1$ NP (+) plants inoculated with the Arkansas and 10W pakchoy isolates and one hundred thirty-nine $R_1$ NP(+) plants inoculated with the Begonia isolate. Numbers above bars represent total numbers of $R_1$ NP(+) plants tested.

EXAMPLE I

Isolation of TSWV-BL RNAs

The TSWV-BL isolate was purified from *Datura stramonium* L. as follows: the infected tissues were ground in a Waring Blender for 45 sec with three volumes of a butter (0.033 M $KH_2PO_4$, 0.067 M $K_6HPO_4$, 0.01 M $Na_2SO_3$). The homogenate was filtered through 4 layers of cheesecloth moistened with the above buffer and centrifuged at 7,000 rpm for 15 min. The pellet was resuspended in an amount of 0.01 M $Na_2SO_3$ equal to the original weight of tissue and centrifuged again at 8,000 rpm for 15 min. After the supernatant was resuspended in an amount of 0.01 M $Na_2SO_3$ equal to 1/10 of the original tissue weight, the virus extract was centrifuged at 9,000 rpm for 15 min. and the supernatant was carefully loaded on a 10–40% sucrose step gradient made up in 0.01 M $Na_2SO_3$. After centrifugation at 23,000 rpm for 35 min., the virus zone (about 3 cm below meniscus) was collected and diluted with two volumes of 0.01 M $Na_2SO_3$. The semi-purified virus was pelleted at 27,000 rpm for 55 min.

EXAMPLE II

Purification of TSWV and Viral RNAs

The TSWV-BL isolate [see Plant Disease 74:154 (1990)] was purified from *Datura stramonium* L, as described in Example I. The purified virus was resuspended in a solution of 0.04% of bentonite, 10 µg/ml of proteinase K, 0.1 M ammonium carbonate, 0.1% (w/v) of sodium diethyldithiocarbanate, 1 mM EDTA, and 1% (w/v) of sodium dodecyl sulfate (SDS), incubated at 65° C. for 5 min., and immediately extracted from $H_2O$-saturated phenol, followed by another extraction with chloroform/isoamyl alcohol (24:1). Viral RNAs were precipitated in 2.5 volumes of ethanol and dissolved in distilled $H_2O$.

EXAMPLE III cDNA and PCR-Based NP Gene Cloning

The first strand cDNA was synthesized from purified TSWV-BL RNAs using random primers as described by Gubler and Hoffman [see Gene 25:263 (1983)]. The second strand was produced by treatment of the sample with RNase H/DNA polymerase. The resulting double-stranded cDNA sample was size-fractionated by sucrose gradient centrifugation, methylated by EcoRI methylase, and EcoRI linkers were added. After digestion with EcoRI, the cDNA sample was ligated into the EcoRI site of pUC18, whose 5'-terminal phosphate groups were removed by treatment with calf intestinal alkaline phospotase. *E. coli* DH5 α competent cells (Bethesda Research Laboratories) were transformed and clones containing TSWV cDNA inserts were first selected by planting on agar plates containing 50 µg/ml of ampicillin, 1PTG, and X-gal. Plasmid DNAs from selected clones were isolated using an alkaline lysis procedure [see BRL Focus 11:7 (1989)], and the insert sizes were determined by EcoRI restriction enzyme digestion followed by DNA transfer onto GeneScreen Plus nylon filters (DuPont). Plasmid clones that contained a TSWV-BL S RNA cDNA insert were identified as described below by hybridizing against a $^{32}$P-labelled oligomer (AGCAGGCAAAACTCGCAGAACTTGC) (SEQ. ID. No.1) complementary to the nucleotide sequence (GCAAGTTCTGCGAGTTTTGCCTGCT) (SEQ. ID. No.2) of the TSWV-CPNH1 S RNA [see J. Gen. Virol. 71:001 (1990)]. Several clones were identified and analyzed on agarose gels to determine the insert sizes. The clone pTSWVS-23 was found to contain the largest cDNA insert, about 1.7 kb in length.

The full-length NP gene was obtained by the use of polymerase chain reaction (PCR). First-strand cDNA synthesis was carried out at 37° C. for 30 min. in a 20 µl reaction mixture using oligomer primer JLS90-46 (5'→3') AGCTAACCATGGTTAAGCTCACTAAGGAAAGC) (SEQ. ID. No.3) (also used to synthesize the nucleocapsid gene of TSWV-10W) which is complementary to the S RNA in the 5' terminus of TSWV NP gene (nucleotide positions 2751 to 2772 of the TSWV-CPNH1). The reaction mixture contained 1.5 µg of viral RNAs, 1 µg of the oligomer primer, 0.2 mM of each dNTP, 1X PCR buffer (the GeneAmp kit, Perkin-Elmer-Cetus), 20U of RNAs in Ribonuclease inhibitor (Promega), 2.5 mM of MgCl$_2$, and 25U of AMV reverse transcriptase (Promega Corporation). The reaction was terminated by heating at 95° C. for 5 min. and cooled on ice. Then 10 µl of the cDNA/RNA hybrid was used to PCR-amplify the NP gene according to manufacturer's instructions (Perkin-Elmer-Cetus) using 1 µg each of oligomer primers JLS90-46 and JLS90-47 (5'→3'), AGCATTCCATGGTTAACACACTAAGCAAGCAC) (SEQ. ID. No.4) (also used to synthesize the nucleotide gene of TSWV-10W), the latter oligomer being identical to the S RNA in the 3' noncoding region of the gene (nucleotide positions 1919 to 1938 of the TSWV-CPNH1). A typical PCR cycle was 1 min. at 92° C. (denaturing), 1 min. at 50° C. (annealing), and 2 min. at 72° C. (polymerizing). The sample was directly loaded and separated on a 1.2% agarose gel. The separated NP gene fragment was extracted from the agarose gel, ethanol-precipitated and dissolved in 20 µl of distilled H$_2$O.

EXAMPLE IV

Construction of Plant Expression and Transformation Vectors

The gel-isolated NP gene fragment from Example III was digested with the restriction enzyme NcoI in 50 µl of a reaction buffer [50 mM Tris-HCl (pH 8.0), 10 mM MgCl$_2$, 0.1 M NaCl] at 37° C. for 3 hours, and directly cloned into NcoI-digested plant expression vector pB1525. The resulting plasmids were identified and designated as pB1525-NP$^+$ in the sense orientation relative to the cauliflower mosaic virus (CaMV) 35S promoter, and as pB1525-NP$^-$ in the reverse orientation. The ability of this expression cassette to produce the NP was determined by transient expression of the NP gene in *Nicotiana tobacum* protoplasts, as described by Pang et al [see Gene 112:229 (1992)]. The expression cassette containing the NP gene was then excised from pB1525-NP$^+$ by a partial digestion with HindIII/EcoRI (since the NP gene contains internal HindIII and EcoRI sites), and ligated into the plant transformation vector pBIN19 (Clontech Laboratories, Inc.) that had been cut with the same enzymes. The resulting vector, pBIN19-NP$^+$ and the control plasmid pBIN19 were transferred to *A. tumefaciens* strain LBA4404, using the procedure described by Holsters et al [see Mol. Gen. Genet. 163:181 (1978)].

Nucleotide sequence analyses of the inserts in clones pTSWV-23 and Pb1525-NP$^+$were determined using the dideoxyribonucleotide method, T7 polymerase (U.S. Biochemicals, Sequenase™), and the double-stranded sequencing procedure described by Siemieniak et al [see Analyt. Biochem. 192:441 (1991)]. Nucleotide sequences were determined from both DNA strands and this information was compared with the published sequences of TSWV isolates CPNH1 using computer programs available from the Genetics Computer Group (GCG, Madison, Wis.).

Transient expression of the NP gene in tobacco protoplasts were also prepared. Plasmid DNAs for clones pTSWVS-23 and pUC18cpphas TSWV-NP (containing the PCR-engineered NP gene insert) were isolated using the large scale alkaline method. The PCR-engineered NP gene insert was excised from clone pBIS25-NP$^+$ by NcoI digestion to take advantage of the available flanking oligomer primers for sequencing. The expression cassette pUC18cpphas is similar to pUC18cpexp except that it utilizes the poly(Å) addition signal derived from the *Phaseolus volgaris* seed storage gene phaseolin. These plasmid DNAs were subjected to two CsCl-ethidium bromide gradient bandings, using a Beckman Tl 70.1 fixed angle rotor. DNA sequences were obtained using dideoxyribonucleotides and the double-stranded plasmid DNA sequencing procedure described above. Nucleotide sequence reactions were electrophoresed on one-meter long thermostated (55° C.) sequencing gels and nucleotide sequence readings averaging about 750 bp were obtained. Nucleotide sequences were determined from both DNA strands of both cloned inserts to ensure accuracy. Nucleotide sequence information from the TSWV-BL S RNA isolate was compared as discussed below, with TSWV isolates CPNH1 and L3 using computer programs (GCG, Madison, Wis.).

The nucleotide and deduced amino acid sequences of cloned cDNA and PCR-engineered insert of TSWV-BL S RNA and their comparison with the nucleotide sequence of TSWV-CPHN1 S RNA are shown below. The nucleotide sequence of the TSWV-BL S RNA clones pTSWVS-23 (TSWV-23) and pB1525-NP$^+$ (TSWV-PCR) were obtained using the double-stranded dideoxynucleotide sequencing procedure of Siemienlak, and their sequences are compared with the relevant regions of the nucleotide sequence of the TSWV-CPNH1 S RNA reported in GeneBank Accession No. D00645. The nucleotide sequence of TSWV-CPNH1 S RNA has been reported by De Haan (1990) and is represented by the following sequence (SEQ. ID. No.5):

```
CAAGTTGAAA GCAACAACAG AACTGTAAAT TCTCTTGCAG TGAAATCTCT GCTCATGTCA    60

GCAGAAAACA ACATCATGCC TAACTCTCAA GCTTCCACTG ATTCTCATTT CAAGCTGAGC   120

CTCTGGCTAA GGGTTCCAAA GGTTTTGAAG CAGGTTTCCA TTCAGAAATT GTTCAAGGTT   180

GCAGGAGATG AAACAAACAA AACATTTTAT TTATCTATTG CCTGCATTCC AAACCATAAC   240

AGTGTTGAGA CAGCTTTAAA CATTACTGTT ATTTGCAAGC ATCAGCTCCC AATTCGCAAA   300

TGCAAAGCTC CTTTTGAATT ATCAATGATG TTTTCTGATT TAAAGGAGCC TTACAACATT   360

GTTCATGACC CTTCATACCC CAAAGGATCG GTTCCAATGC TCTGGCTCGA AACTCACACA   420

TCTTTGCACA AGTTCTTTGC AACTAACTTG CAAGAAGATG TAATCATCTA CACTTTGAAC   480

AACCTTGAGC TAACTCCTGG AAAGTTAGAT TTAGGTGAAA GAACCTTGAA TTACAGTGAA   540

GATGCCTACA AAAGGAAATA TTTCCTTTCA AAAACACTTG AATGTCTTCC ATCTAACACA   600
```

-continued

```
CAAACTATGT CTTACTTAGA CAGCATCCAA ATCCCTTCAT GGAAGATAGA CTTTGCCAGA    660

GGAGAAATTA AAATTTCTCC ACAATCTATT TCAGTTGCAA AATCTTTGTT AAAGCTTGAT    720

TTAAGCGGGA TCAAAAGAA AGAATCTAAG GTTAAGGAAG CGTATGCTTC AGGATCAAAA    780

TAATCTTGCT TTGTCCAGCT TTTTCTAATT ATGTTATGTT TATTTTCTTT CTTTACTTAT    840

AATTATTTCT CTGTTTGTCA TCTCTTTCAA ATTCCTCCTG TCTAGTAGAA ACCATAAAAA    900

CAAAAAATAA AAATGAAAAT AAAATTAAAA TAAAATAAAA TCAAAAAATG AAATAAAAAC    960

AACAAAAAAT TAAAAAACGA AAAACCAAAA AGACCCGAAA GGGACCAATT TGGCCAAATT   1020

TGGGTTTTGT TTTTGTTTTT TGTTTTTTGT TTTTTATTTT TTATTTTATT TTTATTTTAT   1080

TTTATTTTTA TTTTATTTTT ATTTTATTTA TTTTTTGTTT TCGTTGTTTT TGTTATTTTA   1140

TTATTTATTA AGCACAACAC ACAGAAAGCA AACTTTAATT AAACACACTT ATTTAAAATT   1200

TAACACACTA AGCAAGCACA AGCAATAAAG ATAAAGAAAG CTTTATATAT TTATAGGCTT   1260

TTTTATAATT TAACTTACAG CTGCTTTCAA GCAAGTTCTG CGAGTTTTGC CTGCTTTTTA   1320

ACCCCGAACA TTTCATAGAA CTTGTTAAGA GTTTCACTGT AATGTTCCAT AGCAACACTC   1380

CCTTTAGCAT TAGGATTGCT GGAGCTAAGT ATAGCAGCAT ACTCTTTCCC CTTCTTCACC   1440

TGATCTTCAT TCATTTCAAA TGCTTTGCTT TTCAGGACAG TGCAAACTTT TCCTAAGGCT   1500

TCCTTGGTGT CATACTTCTT TGGGTCGATC CCGAGGTCCT TGTATTTTGC ATCCTGATAT   1560

ATAGCCAAGA CAACACTGAT CATCTCAAAG CTATCAACTG AAGCAATAAG AGGTAAGCTA   1620

CCTCCCAGCA TTATGGCAAG TCTCACAGAC TTTGCATCAT CGAGAGGTAA TCCATAGGCT   1680

TGAATCAAAG GATGGGAAGC AATCTTAGAT TTGATAGTAT TGAGATTCTC AGAATTCCCA   1740

GTTTCTTCAA CAAGCCTGAC CCTGATCAAG CTATCAAGCC TTCTGAAGGT CATGTCAGTG   1800

CCTCCAATCC TGTCTGAAGT TTTCTTTATG GTAATTTTAC CAAAAGTAAA ATCGCTTTGC   1860

TTAATAACCT TCATTATGCT CTGACGATTC TTTAGGAATG TCAGACATGA AATAACGCTC   1920

ATCTTCTTGA TCTGGTCGAT GTTTTCCAGA CAAAAAGTCT TGAAGTTGAA TGCTACCAGA   1980

TTCTGATCTT CCTCAAACTC AAGGTCTTTG CCTTGTGTCA ACAAAGGAAC AATGCTTTCC   2040

TTAGTGAGCT TAACCTTAGA CATGATGATC GTAAAAGTTG TTATATGCTT TGACCGTATG   2100

TAACTCAAGG TGCGAAAGTG CAACTCTGTA TCCCGCAGTC GTTTCTTAGG TTCTTAATGT   2160

GATGATTTGT AAGACTGAGT GTTAAGGTAT GAACACAAAA TTGACACGAT TGCTCT       2216
```

The incomplete deduced amino acid sequence of the nonstructural protein gene on TSWV-CPNH1 S RNA is provided below beginning with nucleic acid at position 1 and ending with the nucleic acid codon ending at position 783 (SEQ. ID. No.7).

```
Gln Val Glu Ser Asn Asn Arg Thr Val Asn Ser Leu Ala Val Lys Ser
1               5                   10                  15

Leu Leu Met Ser Ala Glu Asn Asn Ile Met Pro Asn Ser Gln Ala Ser
            20                  25                  30

Thr Asp Ser His Phe Lys Leu Ser Leu Trp Leu Arg Val Pro Lys Val
            35                  40                  45

Leu Lys Gln Val Ser Ile Gln Lys Leu Phe Lys Val Ala Gly Asp Glu
            50                  55                  60

Thr Asn Lys Thr Phe Tyr Leu Ser Ile Ala Cys Ile Pro Asn His Asn
65                  70                  75                  80

Ser Val Glu Thr Ala Leu Asn Ile Thr Val Ile Cys Lys His Gln Leu
            85                  90                  95
```

```
Pro Ile Arg Lys Cys Lys Ala Pro Phe Glu Leu Ser Met Met Phe Ser
            100                 105                 110

Asp Leu Lys Glu Pro Tyr Asn Ile Val His Asp Pro Ser Tyr Pro Lys
        115                 120                 125

Gly Ser Val Pro Met Leu Trp Leu Glu Thr His Thr Ser Leu His Lys
        130                 135                 140

Phe Phe Ala Thr Asn Leu Gln Glu Asp Val Ile Ile Tyr Thr Leu Asn
145                 150                 155                 160

Asn Leu Glu Leu Thr Pro Gly Lys Leu Asp Leu Gly Glu Arg Thr Leu
                165                 170                 175

Asn Tyr Ser Glu Asp Ala Tyr Lys Arg Lys Tyr Phe Leu Ser Lys Thr
            180                 185                 190

Leu Glu Cys Leu Pro Ser Asn Thr Gln Thr Met Ser Tyr Leu Asp Ser
        195                 200                 205

Ile Gln Ile Pro Ser Trp Lys Ile Asp Phe Ala Arg Gly Glu Ile Lys
        210                 215                 220

Ile Ser Pro Gln Ser Ile Ser Val Ala Lys Ser Leu Leu Lys Leu Asp
225                 230                 235                 240

Leu Ser Gly Ile Lys Lys Lys Glu Ser Leu Val Lys Glu Ala Tyr Ala
                245                 250                 255

Ser Gly Ser Lys
            260
```

The nucleotide sequence for TSWV-23 depicted below compares closely with the TWSV sequence given above, and contains one-half of the nonstructural gene and one half of the nucleocapsid protein gene (SEQ. ID. No.6).

```
            AAATTCTCTT GCAGTGAAAT CTCTGCTCAT GTTAGCAGAA AACAACATCA    50
            TGCCTAACTC TCAAGCTTTT GTCAAAGCTT CTACTGATTC TAATTTCAAG   100
            CTGAGCCTCT GGCTAAGGGT TCCAAAGGTT TTGAAGCAGA TTTCCATTCA   150
            GAAATTGTTC AAGGTTGCAG GAGATGAAAC AAATAAAACA TTTTATTTAT   200
            CTATTGCCTG CATTCCAAAC CATAACAGTG TTGAGACAGC TTTAAACATT   250
            ACTGTTATTT GCAAGCATCA GCTCCCAATT CGTAAATGTA AAACTCCTTT   300
            TGAATTATCA ATGATGTTTT CTGATTTAAA GGAGCCTTAC AACATTATTC   350
            ATGATCCTTC ATATCCCCAA AGGATTGTTC ATGCTCTGCT TGAAACTCAC   400
            ACATCTTTTG CACAAGTTCT TTGCAACAAC TTGCAAGAAG ATGTGATCAT   450
            CTACACCTTG AACAACCATG AGCTAACTCC TGGAAAGTTA GATTTAGGTG   500
            AAATAACTTT GAATTACAAT GAAGACGCCT ACAAAAGGAA ATATTTCCTT   550
            TCAAAAACAC TTGAATGTCT TCCATCTAAC ATACAAACTA TGTCTTATTT   600
            AGACAGCATC CAAATCCCTT CCTGGAAGAT AGACTTTGCC AGGGGAGAAA   650
            TTAAAATTTC TCCACAATCT ATTTCAGTTG CAAATCTTTT GTTAAATCTT   700
            GATTTAAGCG GGATTAAAAA GAAAGAATCT AAGATTAAGG AAGCATATGC   750
            TTCAGGATCA AAATGATCTT GCTGTGTCCA GCTTTTTCTA ATTATGTTAT   800
            GTTTATTTTC TTTCTTTACT TATAATTATT TTTCTGTTTG TCATTTCTTT   850
            CAAATTCCTC CTGTCTAGTA GAAACCATAA AACAAAAAT AAAAATAAAA   900
            TAAAATCAAA ATAAAATAAA AATCAAAAAA TGAAATAAAA GCAACAAAAA   950
            AATTAAAAAA CAAAAAACCA AAAAGATCC CGAAAGGACA ATTTTGGCCA  1000
```

-continued

```
AATTTGGGGT TTGTTTTTGT TTTTTGTTTT TTTGTTTTTT GTTTTTATTT    1050
TTATTTTTAT TTTTATTTTT ATTTTATTTT ATTTTATGTT TTTGTTGTTT    1100
TTGTTATTTT GTTATTTATT AAGCACAACA CACAGAAAGCA AACTTTAAT    1150
TAAACACACT TATTTAAAAT TTAACACACT AAGCAAGCACA AACAATAAA    1200
GATAAAGAAA GCTTTATATA TTTATAGGCT TTTTTATAAT TTAACTTACA    1250
GCTGCTTTTA AGCAAGTTCT GTGAGTTTTG CCTGTTTTTT AACCCCAAAC    1300
ATTTCATAGA ACTTGTTAAG GGTTTCACTG TAATGTTCCA TAGCAATACT    1350
TCCTTTAGCA TTAGGATTGC TGGAGCTAAG TATAGCAGCA TACTCTTTCC    1400
CCTTCTTCAC CTGATCTTCA TTCATTTCAA ATGCTTTTCT TTTCAGCACA    1450
GTGCAAACTT TTCCTAAGGC TTCCCTGGTG TCATACTTCT TTGGGTCGAT    1500
CCCGAGATCC TTGTATTTTG CATCCTGATA TATAGCCAAG ACAACACTGA    1550
TCATCTCAAA GCTATCAACT GAAGCAATAA GAGGTAAGCT ACCTCCCAGC    1600
ATTATGGCAA GCCTCACAGA CTTTGCATCA TCAAGAGGTA ATCCATAGGC    1650
TTGAATCAAA GGGTGGGAAG CAATCTTAGA TTTGATAGTA TTGAGATTCT    1700
CAGAATTCC                                                  1709
```

The nucleic acid sequence for TSWV-PCR according to the present invention as depicted below as compares closely with the TSWV sequence given above and covers the whole nucleocapsid protein gene (SEQ. ID. No.8).

```
                    TTAACACACT AAGCAAGCAC AAACAATAAA GATAAAGAAA GCTTTATATA     50
                    TTTATAGGCT TTTTTATAAT TTAACTTACA GCTGCTTTTA AGCAAGTTCT    100
                    GTGAGTTTTG CCTGTTTTTT AACCCCAAAC ATTTCATAGA ACTTGTTAAG    150
                    GGTTTCACTG TAATGTTCCA TAGCAATACT TCCTTTAGCA TTAGGATTGC    200
                    TGGAGCTAAG TATAGCAGCA TACTCTTTCC CCTTCTTCAC CTGATCTTCA    250
                    TTCATTTCAA ATGCTTTTCT TTTCAGCACA GTGCAAACTT TTCCTAAGGC    300
                    TTCCCTGGTG TCATACTTCT TTGGGTCGAT CCCGAGATCC TTGTATTTTG    350
                    CATCCTGATA TATAGCCAAG ACAACACTGA TCATCTCAAA GCTATCAACT    400
                    GAAGCAATAA GAGGTAAGCT ACCTCCCAGC ATTATGGCAA GCCTCACAGA    450
                    CTTTGCATCA TCAAGAGGTA ATCCATAGGC TTGACTCAAA GGGTGGGAAG    500
                    CAATCTTAGA TTTGATAGTA TTGAGATTCT CAGAATTCCC AGTTCCTCA    550
                    ACAAGCCTGA CCCTGATCAA GCTATCAAGC CTTCTGAAGG TCATGTCAGT    600
                    GGCTCCAATC CTGTCTGAAG TTTTCTTTAT GGTAATTTTA CCAAAAGTAA    650
                    AATCGCTTTG CTTAATAACC TTCATTATGC TCTGACGATT CTTCAGGAAT    700
                    GTCAGACATG AAATAATGCT CATCTTTTTG ATCTGGTCAA GGTTTTCCAG    750
                    ACAAAAAGTC TTGAAGTTGA ATGCTACCAG ATTCTGATCT TCCTCAAACT    800
                    CAAGGTCTTT GCCTTGTGTC AACAAAGCAA CAATGCTTTC CTTAGTGAGC    850
                    TTAACCAT                                                  858
```

Together the cloned TSWV-23 insert overlaps the TSWV-PCR insert, and together they represent the 2028 nucleotides of the TSWV-BL S RNA according to the present invention.

This 2028 nucleotide sequence according to the present invention contains a part of the nonstructural gene and whole nucleocapsid protein gene. The combined sequence is (SEQ. ID. No.9).

```
AAATTCTCTT GCAGTGAAAT CTCTGCTCAT GTTAGCAGAA AACAACATCA    50
TGCCTAACTC TCAAGCTTTT GTCAAAGCTT CTACTGATTC TAATTTCAAG   100
CTGAGCTTCT GGCTAAGGGT TCCAAAGGTT TTGAAGCAGA TTTCCATTCA   150
GAAATTGTTC AAGGTTGCAG GAGATGAAAC AAATAAAACA TTTTATTTAT   200
CTATTGCCTG CATTCCAAAC CATAACAGTG TTGAGACAGC TTTAAACATT   250
ACTGTTAGTT GCAAGCATCA GCTCCCAATT CGTAAATGTA AAACTCCTTT   300
TGAATTATCA ATGATGTTTT CTGATTTAAA GGAGCCTTAC AACATTATTC   350
ATGATCCTTC ATATCCCCAA AGGATTGTTC ATGCTCTGCT TGAAACTCAC   400
ACATCTTTTG CACAAGTTCT TTGCAACAAC TTGCAAGAAG ATGTGATCAT   450
CTACACCTTG AACAACCATG AGCTAACTCC TGGAAAGTTA GATTTAGGTG   500
AAATAACTTT GAATTACAAT GAAGACGCCT ACAAAAGGAA ATATTTCCTT   550
TCAAAAACAC TTGAATGTCT TCCATCTAAC ATACAAACTA TGTCTTATTT   600
AGACAGCATC CAAATCCCTT CCTGGAAGAT AGACTTTGCC AGGGGAGAAA   650
TTAAAATTTC TCCACAATCT ATTTCAGTTG CAAAATCTTT GTTAAATCTT   700
GATTTAAGCG GGATTAAAAA GAAAGAATCT AAGATTAAGG AAGCATATGC   750
TTCAGGATCA AAATGATCTT GCTGTGTCCA GCTTTTTCTA ATTATGTTAT   800
GTTTATTTTC TTTCTTTACT TATAATTATT TTTCTGTTTG TCATTTCTTT   850
CAAATTCCTC CTGTCTAGTA GAAACCATAA AAACAAAAAT AAAAATAAAA   900
TAAAATCAAA ATAAAATAAA AATCAAAAAA TGAAATAAAA GCAACAAAAA   950
AATTAAAAAA CAAAAAACCA AAAAAGATCC CGAAAGGACA ATTTTGGCCA  1000
AATTTGGGGT TTGTTTTTGT TTTTTGTTTT TTTGTTTTTT GTTTTTATTT  1050
TTATTTTTAT TTTTATTTTT ATTTTATTTT ATTTTATGTT TTTGTTGTTT  1100
TTGTTATTTT GTTATTTATT AAGCACAACA CACAGAAAGC AAACTTTAAT  1150
TAAACACACT TATTTAAAAT TTAACACACT AAGCAAGCAC AAACAATAAA  1200
GATAAAGAAA GCTTTATATA TTTATAGGCT TTTTTATAAT TTAACTTACA  1250
GCTGCTTTTA AGCAAGTTCT GTGAGTTTTG CCTGTTTTTT AACCCCAAAC  1300
ATTTCATAGA ACTTGTTAAG GGTTTCACTG TAATGTTCCA TAGCAATACT  1350
TCCTTTAGCA TTAGGATTGC TGGAGCTAAG TATAGCAGCA TACTCTTTCC  1400
CCTTCTTCAC CTGATCTTCA TTCATTTCAA ATGCTTTTCT TTTCAGCACA  1450
GTGCAAACTT TTCCTAAGGC TTCCCTGGTG TCATACTTCT TTGGGTCGAT  1500
CCCGAGAACC TTGTATTTTG CATCCTGATA TATAGCCAAG ACAACACTGA  1550
TCATCTCAAA GCTATCAACT GAAGCAATAA GAGGTAAGCT ACCTCCCAGC  1600
ATTATGGCAA GCCTCACAGA CTTTGCATCA TCAAGAGGTA ATCCATAGGC  1650
TTGACTCAAA GGGTGGGAAG CAATCTTAGA TTTGATAGTA TTGAGATTCT  1700
CAGAATTCCC AGTTTCCTCA ACAAGCCTGA CCCTGATCAA GCTATCAAGC  1750
CTTCTGAAGG TCATGTCAGT GGCTCCAATC CTGTCTGAAG TTTTCTTTAT  1800
GGTAATTTTA CCAAAAGTAA AATCGCTTTG CTTAATAACC TTCATTATGC  1850
```

```
                                        -continued
TCTGACGATT CTTCAGGAAT GTCAGACATG AAATAATGCT CATCTTTTTG    1900

ATCTGGTCAA GGTTTTCCAG ACAAAAAGTC TTGAAGTTGA ATGCTACCAG    1950

ATTCTGATCT TCCTCAAACT CAAGGTCTTT GCCTTGTGTC AACAAAGCAA    2000

CAATGCTTTC CTTAGTGAGC TTAACCAT                            2028
```

This comparison showed that cDNA insert of clone pTSWVS-23 included about 760 bp of the 52 K protein viral component gene, the complete intergenic region (492 bp), and 450 bp of the NP gene (about half of the NP gene). This cloned insert had its 3'-end located exactly at an EcoRI recognition site, which suggested incomplete EcoRI methylation during the cDNA cloning procedure. Although this clone did not contain the complete TSWV-BL NP gene, its sequence was of considerable importance since it had a 450 bp overlap with the sequence of the PCR-engineered NP gene (a total of 2028 bp of the TSWV-BL S RNA is presented in the nucleotide sequence for TSWV). The sequence comparison between this TSWV-BL PCR-engineered and TSWV-CPNH1 NP genes revealed a total of 21 nucleotide differences (2.7%), eight of which encode amino acid replacements (3.1%). Since this PCR engineered NP gene was obtained using Taq polymerase, which is known to incorporate mutations, it is possible that some of these differences were introduced during PCR amplification. However, 15 of these nucleotide differences were located within the overlapping region between the TSWV-BL cDNA and PCR clones, and all but one of these nucleotide differences (position 1702 of TSWV; position 485 of TSWV-PCR)) are shared by both TSWV-BL S RNA derived clones. This comparison clearly showed that the PCR amplification did not contribute greatly, if at all, to the difference between the nucleotide sequences of these two cloned NP gene regions. The nucleotide difference at position 1702 resulted in the amino acid replacement of Ile with Ser, and even this difference could be due to the lack of homogeneity within the TSWV-BL isolate.

EXAMPLE V

Agrobacterium-Mediated Transformation

Leaf discs of Nicotiana tabacum var Havana cv 423 were inoculated with the Agrobacterium strain LBA4404 (ClonTech) containing the vector pBIN19-NP+ or the control plasmid pBIN19, by soaking overnight in a liquid culture of the Agobacterium, and the inoculated leaf discs were incubated on non-selective MS medium for 3 days. [see Science 227:1229 (1985)]. Transformed cells were selected and regenerated in MS medium containing 300 µg/ml kanamycin and 500 µg/ml carbenicillin for shoot regeneration. Roots were induced after transfer of plantlets to hormone-free medium. Rooted transformants were transferred to soil and grown under greenhouse conditions. The MS medium contains full strength MS salt (Sigma), 30 g/l sucrose, 1 mg/l BA and 1 ml of $B_5$ vitamins [1 mg/ml Nicotinic acid, 10 mg/ml Thiamine (HCl), 1 mg/ml Pyridoxine (HCl), 100 mg/ml myo-Inositol]. Transgenic plants were self-pollinated and seeds were selectively germinated on kanomycin medium.

EXAMPLE VI

Serological Detection of Proteins

Double antibody sandwich enzyme-linked immunosorbent assay (DAS-ELISA) was used to detect the expression of NP gene in transgenic plants with polyclonal antibodies against the TSWV-BL NP. Each sample was prepared by grinding a leaf disc (about 0.05 g) from the top second leaf of the plant in 3 ml of an enzyme conjugate buffer [phosphate-buffered saline, 0.05% Tween 20, 2% polyvinylpyrrolidone 40, and 0.2% ovalbumin]. For tobacco protoplasts, the cell extracts after centrifugation were directly used for the assay. A ten- and three-fold dilutions of the samples from both transgenic plants and tobacco protoplasts were made just before DAS-ELISA.

For Western blots, a leaf disc (about 0.05 g) was ground in 0.25 ml of 2X SDS/sample buffer (0.126 M Tris buffer, 20% glycerol, 2% SDS, 2% 2-mercaptoethanol, and 0.01 mg/ml bromphenol blue). The homogenates were centrifuged and the supernatants were boiled before loading. Proteins (10–20 µl sample/lane) were separated and blotted onto a membrane. The membrane was then processed following the manufacturer's immunoselect kit instruction manual (Gibco BRL Life Technologies Inc.). Antibodies to the whole virion were preabsorbed with cell extracts from health tobacco plants [See Plant Disease' 70:501 (1986)], and were used in Western blot at a concentration of 2 µg/ml.

Serological reactions of TSWV isolates (TSWV-BL, Arkansas, 10W pakchoy, Begonia or Brazil) were assayed in DAS-ELISA using antibodies raised against TSWV-BL virion, or the NP of TSWV-BL or TSWV-I.

EXAMPLE VII

Inoculation of Transgenic Plants with TSWV Isolates

Inocula were prepared by infecting Nicotiana benthamiana Domin. with different TSWV isolates and grinding infected leaves (0.5 g) of N. benthamiana plants (1 to 2 weeks after inoculation) in 15 ml. of a buffer (0.033 M $KH_2PO_4$, 0.067 M $K_2HOP_4$ and 0.01 M $Na_2SO_3$). The inoculum extracts were immediately rubbed on corundum-dusted leaves of transgenic plants and the inoculated leaves were subsequently rinsed with $H_2O$. Because TSWV is highly unstable in vitro after grinding, each batch of inoculum was used to first inoculate NP(+) plants containing the NP gene; the last inoculated plants of each inoculum were always control NP(−) plants containing the vector sequence alone to assure that a particular virus inoculum was still infective at the end of inoculation.

Data on local lesions and systemic infections were taken 7–15 days after inoculation and expressed in the following table as the number of plants systemically infected over the number of plants inoculated, except where indicated. In this table, the data collected under "ELISA" is the data of $R_0$ lines from with the $R_1$ plants were derived; the Begonia isolate induced local lesions on the $R_1$ plants, and the resistance was expressed as the number of plants producing local lesions over the number of plants inoculated; and NT indicates that there was no test.

Reations of $R_1$ plants expressing the nucleocapsid protein (NP) gene of tomato spotted wilt virus (TSWV) to inoculation with TSWV isolates.

| $R_0$ line | ELISA: (R0 pl.) | BL | Arkansas | 10W Pakchov | Begonia | Brazil |
|---|---|---|---|---|---|---|
| NP(+)2 | 0.015 | 0/20 | 4/25 | 3/24 | 29/40 | 36/36 |
| NP(+)4 | 0.386 | 6/30 | 21/23 | 18/21 | 9/48 | 42/42 |
| NP(+)9 | 0.327 | 0/20 | NT | 20/20 | — | — |
| NP(+)14 | 0.040 | 0/20 | — | 9/20 | 8/18 | 18/18 |
| NP(+)21 | 0.042 | 0/15 | 5/15 | 3/15 | 2/4 | 6/6 |
| NP(+)22 | 0.142 | 0/20 | — | 15/20 | 31/36 | 36/36 |
| NP(+)23 | 0.317 | 0/20 | — | 16/20 | — | — |
| NP(−) | — | 42/42 | 24/24 | 62/62 | 66/66 | 54/54 |

As described above, the isolation of the TSWV-BL NP gene, which resides in the S RNA component of TSWV, was approached using two strategies. The cDNA cloning strategy yielded several clones containing cDNA inserts derived from TSWV-BL S RNA, as identified by hybridization against an oligomer probe complementary to the TSWV-CPNH1 S RNA. Clone pTSWVS-23 contained the longest insert, which mapped at about 1.7 kb in length. The second strategy utilized the published sequence of TSWV-CPNH1 S RNA and PCR to amplify and engineer the NP gene for expression directly from total TSWV-BL RNA. Oligomer primers JLS90-46 and -47 were synthesized, with JLS90-46 being complementary to the S RNA in the 5'-coding region of the NP gene (positions 2051–2073 of the TSWV-CPNH1) while JLS90-47 being of the 3'-noncoding region of the NP gene (positions 1218 to 1237 of the TSWV-CPNH1). Both of the primers contain the recognition site for the restriction enzyme NcoI for subsequent cloning, and the primer JLS90-46 has a plant consensus translation initiation codon sequence (AAXXATGG), which upon amplification was expected to fuse the translation initiation codon to the third codon (GTT) of the NP gene. Fusion of the translation initiation codon to the third codon of the TSWV-BL NP gene was done to preserve the NcoI recognition site while not incorporating any amino acid codons. Thus, expression of the PCR-engineered TSWV NP gene would yield a TSWV-BL NP that was two amino acids (Ser-Lys) shorter at the N-terminus than the native NP.

This specifically-amplified DNA fragment, of about 850 bp, was digested with NcoI and cloned into the plant expression vector pB1525. The orientation of the TSWV-BL NP gene with respect to the CaMV 35S promoter was determined by restriction enzyme site mapping (EcoRI, HindIII, AvaI and AlWNI). Several clones were isolated that contain the insert in the proper orientation (pB1525-NP$^+$) and others that contain the insert in the opposite orientation (pB1525-NP$^−$). This restriction enzyme site mapping data also showed that the inserts of clones pB1525-NP$^+$ contained restriction enzyme sites that were identical to those found in the TSWV-CPNH1 NP gene. The expression of TSWV-BL NP gene was thus controlled by a double CaMV 35S promoter fused to the 5'-untranslated leader sequence of alfalfa mosaic virus (ALMV) of the expression vector pB1525. Expression vectors that utilize the stacked double CaMV 35S promoter elements yield higher levels of mRNA transcription than similar vectors that utilize a single 35S promoter element.

Three pB1525-NP$^+$ clones were transiently expressed in tobacco protoplasts to confirm that the amplified DNA fragment encoded the NP. To achieve this, the clones were transferred into tobacco protoplasts by the PEG method, and after two days of incubation the expressed NP was detected by DAS-ELISA using antibodies against the whole TSWV-BL virion. High levels of NP were produced in tobacco protoplasts harboring the NP gene in plasmid pB1525-NP$^+$; while no NP was detected in tobacco protoplasts transformed with the antisense NP sequence (pB1525-NP$^−$).

As described previously, the PCR-engineered insert of clone pB1525-NP$^+$ and the cDNA insert of the clone pTSWV-23 were subjected to double stranded sequencing. The sequence analysis of the cDNA and the PCR clones revealed inserts of 1.71 kb and 865 bp, respectively which, when compared with the sequence TSWV-CPNH1 S RNA, shows that cDNA insert of cone pTSWV-23 includes about 760 bp of the 52 K protein viral component gene, the complete intergenic region (492 bp), and 450 bp of the NP gene (about one-half of the gene). This cloned insert has its 3'-end located exactly at an EcoRI recognition site suggesting incomplete EcoRI methylation during the cDNA cloning procedure. Although this clone does not contain the complete TSWV-BL NP gene, its sequence is of considerable importance since it has a 450 bp overlap with the sequence of the PCR-engineered NP gene. The sequence comparison between this TSWV-BL PCR-engineered and, TSWV-CPHN1 NP genes reveals a total of 21 nucleotide differences (2.7%), eight of which encode amino acid replacements (3.1%). Since this PCR-engineered NP gene was obtained using Taq polymerase, which is known to incorporate mutations, it is possible that some of these differences were introduced during PCR amplification. However, 15 of these nucleotide differences are located within the overlapping region between the TSWV-BL cDNA and PCR clones, and all but one of these differences (position 1702) are present in both TSWV-BL S RNA derived clones. This comparison clearly shows that the PCR amplification did not contribute greatly, if at all, to the difference between the nucleotide sequences of these two NP genes. The nucleotide difference at position 1702 results in the amino acid replacement of Ile with Ser, and even this difference could be due to the lack of homogeneity within the TSWV-BL isolate.

The possibility that the nucleotide differences can be attributed to divergence among the TSWV isolates is also supported by comparisons with other sequenced regions among TSWV-CPNH1, TSWV-L3, and TSWV-BL S RNAs.

These comparisons are tabulated below:

Percent nucleotide and amino acid sequence differences for the comparison of TWSV S RNA component from isolates CPNH1, L3 and BL[a]

| | 52 K Protein Gene | | Intergenic | NP Gene | |
|---|---|---|---|---|---|
| Comparison | Nucleotide | Amino Acid | Nucleotide | Nucleotide | Amino Acid |
| CPNH1/L3 | 68/1396[b](4.9)[c] | 49/464(10.6) | 46/511(9.0) | 24/777(3.1) | 4/258(1.6) |
| CPNH1/BL | 21/758(4.1) | 23/251(9.2) | 26/496(5.2) | 19/765(2.5) | 8/255(3.1) |
| L3/BL | 38/765(5.0) | 20/254(7.9) | 38/498(7.6) | 19/767(2.5) | 4/255(1.6) |

[a]Comparisons are made using the sequence information available from the particular component region of TSWV-BL. The comparison for the TSWV-BL NP gene includes the combined sequence information from the cDNA clone, pTSWVS-23 and PCR-engineered insert.
[b]Comparison numbers are total differences (nucleotides or amino acids) divided by total number of positions (nucleotides or amino acids) compared. For both nucleotide and amino acid calculation gaps, regardless of length, were counted as one mismatch.
[c]Numbers in parentheses are percentages.

The nucleotide sequence of the NP genes from the CPNH1 and L3 isolates differ from each other by 3.1% and from the BL isolate by nearly a similar degree (2.5%). However, the NP amino acid sequences between CPNH1 and BL isolates differ by a considerably larger amount than they differ between the L3 and BL or CPNH1 and L3 isolates. The results tabulated above also reveal that the NP gene region of these TSWV isolates is subject to a higher degree of selective pressure than the 52 K protein as the differences among the amino acid sequences of the 52 K protein range between 7.9 to 10.6%, more than twice that found for the amino acid sequence of the NPs. Nucleotide sequence divergence is highest among the intergenic regions, indicating that this region is subject to less selective pressure than either genetic region.

The presence of NP gene sequences in transgenic plants was first confirmed by PCR analysis. A NP DNA fragment of about 800 bp was specifically amplified from the total DNAs of transgenic NP(+) plants using the primers homologous to sequences flanking the NP gene, whereas no corresponding fragment was detected in control NP(−) plants. Expression of the NP gene was assayed in each $R_0$ transgenic plant by DAS-ELISA, and the results are presented in the following table:

Reactions of R0 transgenic plants expressing the nucleocapsid protein (NP) gene of tomato spotted wilt virus (TSWV) to inoculation with TSWV-BL isolate

| plant age | $R_0$ clone | ELISA[a] | Lesions/leaf[b] | NP(+):NP(−)[c] |
|---|---|---|---|---|
| 7–8 leaves: | NP(+)1 | 0.374 | 7 (199) | 1:28 |
| | NP(+)2 | 0.015 | 0 (199) | 0:199 |
| | NP(+)3 | 0.407 | 23 (102) | 1:4 |
| | NP(+)4 | 0.386 | 2 (102) | 1:51 |
| | NP(+)5 | 0.023 | 0 (124) | 0:124 |
| | NP(+)6 | 0.197 | 35 (325) | 1:9 |
| | NP(+)7 | 0.124 | 1 (325) | 1:325 |
| 9–10 leaves: | NP(+)8 | 0.344 | 36 (36) | 1:1 |
| | NP(+)9 | 0.327 | 2 (20) | 1:10 |
| | NP(+)10 | 0.406 | 34 (33) | 1:1 |
| | NP(+)11 | 0.156 | 5 (20) | 1:4 |
| | NP(+)12 | 0.133 | 9 (57) | 1:6 |
| | NP(+)13 | 0.144 | 2 (7) | 1:4 |
| | NP(+)14 | 0.040 | 0 (19) | 0:19 |
| | NP(+)16 | 0.053 | 0 (10) | 0:10 |

-continued

Reactions of R0 transgenic plants expressing the nucleocapsid protein (NP) gene of tomato spotted wilt virus (TSWV) to inoculation with TSWV-BL isolate

| plant age | $R_0$ clone | ELISA[a] | Lesions/leaf[b] | NP(+):NP(−)[c] |
|---|---|---|---|---|
| 5–6 leaves: | NP(+)20 | 0.487 | 203 (117) | 2:1 |
| | NP(+)21 | 0.042 | 0 (117) | 0:117 |
| | NP(+)22 | 0.142 | 0 (208) | 0:208 |
| | NP(+)23 | 0.317 | 223 (208) | 1:1 |
| | NP(+)24 | 0.051 | 0 (35) | 0:35 |
| | NP(+)25 | 0.286 | 13 (35) | 1:3 |
| | NP(+)26 | 0.037 | 0 (22) | 0:22 |
| | NP(+)27 | 0.425 | 305 (22) | 14:1 |

[a]production of the NP in transgenic plants was assayed by double antibody sandwich enzyme-linked immunosorbent assay (DAS-ELISA); concentration of antibodies against virion for coating: 1 μg/ml; dilution of conjugate to the NP of TSWV-BL: 1:250; results taken 150 min. after adding substrate; readings at 405 nm.
[b]local lesions that developed on inoculated leaves were counted 7 days after inoculation. Data represent the average of three inoculated leaves. Data in parentheses are the number of lesions produced from control NP(−) plants inoculated with the same inoculum.
[c]the ratio of local lesions that developed on NP(+) plants transformed with pBIN19-NP[+] versus local lesions that developed on the control NP (−) plant when inoculated with the same inoculum.

Of the 23 NP(+) clones, 10 produced high levels of NP, 5 accumulated intermediate levels of NP, and the remaining 8 produced low levels of NP. The size of the NP expressed in transgenic plants was analyzed using Western blot. Many polypeptides from tobacco extracts were reactive to the antibodies against the whole virion even though the antibodies were pre-absorbed with extracts from healthy tobacco plants. Of those, only one band was unique to the pattern of polypeptides from tobacco plants transformed with the NP gene. This polypeptide was estimated to be around 29 kDa, which is near the expected size of the native NP. No antibody reactive-protein band of similar size was found in extracts from transgenic plants containing the vector pBIN19.

Inoculation of tobacco leaves with TSWV-BL isolate could result in either systemic infection or necrotic local lesions, depending upon weather conditions and physiological stages of plants. When $R_0$ plants were tested with TSWV-BL for viral resistance, TSWV-BL induced typical necrotic lesions on the inoculated leaves of control NP(−) plants 6–8 days after inoculation. However, transgenic NP(+) plants showed a spectrum of resistance to the virus when compared to control NP(−) plants. Eleven of the 23

NP(+) plants did not develop any local lesion or the number of lesions that developed was at least 20-fold less than that on the corresponding inoculated NP(−) plants. Three NP(+) plants had intermediate reactions (5- to 19-fold less lesions than controls) while the remaining 9 plants had low or no resistance. None of the inoculated NP(+) or NP(−) plants showed systemic infection. Symptomless $R_0$ plants were monitored until the end of their life cycle, and no symptom was observed throughout their life cycles. The inoculated leaves of the symptomless NP(+) plants were checked for the presence of the virus on the leaves of $C_1$ quinoa plants No virus was recovered from TSWV-BL-challenged leaves of highly resistant NP(+) plants, suggesting that the virus could not replicate or spread in these NP(+) plants.

Leaf discs from selected $R_0$ plants were subcloned, and the regenerated plantlets were challenged by the virus. All subcloned $R_0$ plants displayed levels of resistance similar to their corresponding original $R_0$ plants.

Since TSWV is widespread and many biologically distant strains exist, the effectiveness of the transgenic plants to resist infections by different TSWV isolates were also tested. Five TSWV isolates were chosen in this study to challenge R1 plants germinated on kanamycin-containing medium: TSWV-BL, Arkansas, 10W pakchoy, Begonia and Brazil. The first three isolates were reactive to the antibodies against the whole virion and the NP of TSWV-BL (the common TSWV "L" serogroup) (see FIG. 5). Begonia isolate reacted strongly to the antibodies against the NP of TSWV-I (the "I" serogroup) but not to those raised against the TSWV-BL NP, and therefore belonged to the "I" serogroup. No detectable reaction of Brazil isolate was found to the antibodies against either the NP of the TSWV-BL or the TSWV-I serogroup, and it was weakly reactive to the antibodies against the whole virion of TSWV-BL. Moreover, this isolate caused systemic mottle and crinkle on the leaves of infected tobacco and N. benthamiana, but did not infect squash or cucumbers indicating that it is a distinct isolate from the cucurbit isolate. These results indicate that this isolate may be considered to be a third serogroup.

Seedlings derived from seven $R_0$ lines were germinated on kanamycin medium and inoculated with the above TSWV isolates. Infectivity data were recorded daily starting seven days after inoculation. Plants inoculated with TSWV-BL, Arkansas, 10W pakchoy or Brazil isolates were rated susceptible if virus symptoms were observed on uninoculated leaves. Plants inoculated with the Begonia isolate were rated susceptible if local lesions were observed on inoculated leaves, since this isolate does not cause systemic infection in tobacco. All inoculated control NP(−) $R_1$ plants were susceptible to infection by these five isolates. They were systemically infected 12 days after inoculation except that transgenic $R_1$ plants inoculated with Begonia produced only local lesions on the inoculated leaves. However, almost all NP(+) $R_1$ plants were highly resistant to the homologous isolate TSWV-BL, while much lower percentages of NP(+) $R_1$ plants were resistant to heterologous isolates Arkansas, 10W pakchoy and Begonia. On the other hand, all NP(+) $R_1$ plants from the seven transgenic lines were susceptible to the Brazil isolate, even though a slight delay (1 to 2 days) in symptom expression was observed in some of the high NP-expressing NP(+) $R_1$ plants from line NP(+)4.

Resistant $R_1$ plants remained symptomless throughout their life cycles. The inoculated leaves of seventeen symptomless NP(+) plants were checked for the presence of the virus by back inoculation on leaves of Chenopodium quinoa plants. No virus was recovered from the inoculated leaves of symptomless NP(+) plants, suggesting that the virus could not replicate or spread in these NP(+) plants.

The relationship between the level of NP accumulation in transgenic plants and the degree of resistance to heterologous TSWV isolates was also studied. Analysis of the data described above suggested that $R_1$ plants derived from $R_0$ lines with low levels of NP offered the best resistance to the heterologous isolates of the "L" serogroup (Arkansas and 10W pakchoy) while $R_1$ from a $R_0$ line with high level of NP were resistant to the Begonia isolate, which belongs to the "I" serogroup. For example, an average 76% of inoculated $R_1$ plants from low NP expressing lines NP(+) 2, 14, and 21 were resistant to infections by the Arkansas and 10W pakchoy isolates, while resistance to these isolates was observed in only 11% of similarly inoculated plants from high NP expressing lines NP(+)4, 9, and 23. On the other hand, the Begonia isolate infected 79% of $R_1$ plants from the low NP expressing line NP(+)2, 14, and 21 but only 19% from high NP expressing line NP(+)4.

Therefore, it was concluded that the transgenic $R_1$ plants expressing low levels of the NP gene were highly resistant to infection with the isolate 10W pakchoy (the "L" serogroup), but not to Begonia isolate (the "I" serogroup). In contrast, the highly NP-expressing $R_1$ plants were very resistant to infection by Begonia isolate but not to infection by the isolate from 10W pakchoy.

Thus, it was of interest to accurately quantitate the relation of NP expression in individual plants with resistance to the heterologous isolates. In a number of inoculation experiments reported herein, leaf samples of transgenic plants were taken before inoculating with the Arkansas and 10W pakchoy isolates. Samples were also taken from non-inoculated leaves of plants inoculated with the Begonia isolate after observations of the apparent relation between NP expression levels and resistance were made. The latter method of sampling could be done without interference from infection by the Begonia isolate because this isolate does not cause systemic infection in tobacco nor reacts with antibodies to the TSWV-BL NP. All samples were assayed for relative NP levels by DAS-ELISA using antibodies raised to isolated NP of TSWV-BL. FIGS. 5 and 6 show the relation between NP levels in transgenic $R_1$ plants (irrespective of the $R_0$ lines they came from) and their resistance to the Arkansas and 10W pakchoy isolates or to the Begonia isolate. Nearly all transgenic $R_1$ plants with very low or undetectable ELISA reactions (0–0.05 $OD_{405\ nm}$) were resistant to infections by the Arkansas and 10W pakchoy isolates (the "L" serogroup) but susceptible to the Begonia isolate (the "I" serogroup). In contrast, almost all $R_1$ plants that gave high ELISA reactions (0.4–1.0 $OD_{405\ nm}$) were resistant to the Begonia isolate but susceptible to the Arkansas and 10W pakchoy isolates.

The double-stranded (ds) RNA was isolated from the N. benthamiana plants infected with TSWV-B using a combination of methods [See Acta Horticulturae 186:51 (1986), and Can. Plant Dis Surv 68:93(1988)] which have been successfully used for isolation of dsRNA from tissue infected with grapevine leafroll virus. The dsRNA was chosen for the cDNA synthesis since isolation of the virus particle from this isolate has not been possible [see Plant Disease 74:154 (1990)]. In order to make a cDNA library specific to the S RNA of TSWV-B, the double stranded S RNA was gel-purified, denatured by methyl-mercury treatment, and subjected to cDNA synthesis procedure provided by Promega using random primers. The synthesized cDNA fragments were cloned via an EcoRI adapter into the EcoRI digested λ ZAPII (Strategene), and positive clones were identified by colony hybridization using the cDNA probes prepared by reverse transcription of gel-purified S RNA. Dozens of positive clones were analyzed on agarose gels and only three overlapping clones containing the largest inserts (L1, L22 and L30) were selected (see FIG. 3), covering nearly entire TSWV-B S RNA.

The nucleotide sequences of the inserts in clones L1, L22 and L30 were determined from both DNA strands, first by the universal and reverse primers and then by the internal primers designed for sequencing the S RNA of TSWV-B. Sequencing was done using the Sanger dideoxyribonucleotide method, T7 polymerase (U.S. Biochemicals, Sequenase™), and the double-stranded sequencing procedure described by Siemieniak [see Analyt. Biochem. 192:441 (1991)]. The sequence analyses of these clones revealed inserts of 1.994 kb, 2.368 kb and 1.576 kb, respectively, and these sequences represented 93% of the S RNA genome (see FIG. 3). The assembled sequence was analyzed by comparisons with sequences of TSWV isolates CONH1, L3, I, and BL using computer programs available from the Genetics Computer Group (GCG, Madison, Wis.).

Computer analysis showed that the assembled sequence of 2.842 kb covered the complete 52 K nonstructural protein gene, the complete intergenic region (629 bp), and 737 bp of the NP gene (only 39 N-terminal nucleotides of the N gene were not represented). In order to obtain this missing region of the N gene, a primer TTCTGGTCTTCTTCAAACTCA (SEQ. ID. No.10), identical to a sequence 62 nucleotides from the initiation codon of the N gene, was end-labeled with polynucleotide kinase to screen the cDNA library described above. Five putative clones were obtained. Sequence analysis of the five clones showed that only clones S6 and S7 contain these 39 missing nucleotides of the N gene. The latter clone also included the extreme 3' end of the S RNA.

The 5' extreme end of the S RNA was obtained using the 5' RACE System (GIBCO). Both ssRNA of TSWV-B and total RNAs isolated from tobacco plants infected with TSWV-B were used to synthesize first strand cDNA with an oligonucleotide (5'-CTGTAGCCATGAGCAAAG) (SEQ. ID. No.11) complementary to the nucleotide positions 746–763 of the TSWV-B S RNA. The 3'-end of the first strand cDNA was tailed with dCTP using terminal deoxynucleotidyl transferase. Tailed cDNA was then amplified by PCR using an anchor primer that anneals to the homopolymeric tail, and an oligonucleotide (5'-TTATATCTTCTTCTTGGA) (SEQ. ID. No.17) that anneals to the nucleotide positions 512–529 of the TSWV-B S RNA. The PCR-amplified fragment was gel-purified and directly cloned into the T-vector pT7Blue (Novagen) for sequence analysis. Eight independent clones were sequenced with an oligomer primer (5'-GTTCTGAGATTTGCTAGT) (SEQ. ID. No.16) close to the 5' region of the S RNA (nucleotide positions 40–57 of the TSWV-B S RNA). Six of the resulting clones contained the 5' extreme end of the S RNA and the 5'-terminal nucleotide sequence from these clones was identical. Thus, the complete nucleotide sequence of the TSWB-B S RNA is 3049 nucleotides in length.

Thus these two clones together with the three clones previously sequenced (L1, L22, L30, S6 and S7) covered a total of 3032 nucleotides depicted above. Comparisons with the terminal sequences of TSWV-CPNH1 and TSWV-I revealed that although the extreme 5' end of 18 nucleotides was not represented in the assembled sequence, the extreme 3'-terminus of the TSWV-B S RNA is identical to the extreme 3' end of the TSWV-I S RNA and is only one out of fifteen nucleotides different from the extreme 3' end of TSWV-CPNH1. The conservation of the terminal sequence among TSWV isolates is consistent with observations of the other members of *Bunyaviridae* genera, and supports the hypothesis that the terminal sequences might form stable base-paired structure, which could be involved in its replication and encapsulation.

The complete nucleotide sequence of the S RNA genome of TSWV-B (the Brazilian isolate discussed above) according to the present invention is (SEQ. ID. No.14).

```
AGAGCAATTG GGTCATTTTT TATTCTAAAT CGAACCTCAA CTAGCAAATC    50

TCAGAACTGT AATAAGCACA AGAGCACAAG AGCCACAATG TCATCAGGTG   100

TTTATGAATC GATCATTCAG ACAAAGGCTT CAGTTTGGGG ATCGACAGCA   150

TCTGGTAAGT CCATCGTGGA TTCTTACTGG ATTTATGAGT TTCCAACTGG   200

TTCTCCACTG GTTCAAACTC AGTTGTACTC TGATTCGAGG AGCAAAAGTA   250

GCTTCGGCTA CACTTCAAAA ATTGGTGATA TTCCTGCTGT AGAGGAGGAA   300

ATTTTATCTC AGAACGTTCA TATCCCAGTG TTTGATGATA TTGATTTCAG   350

CATCAATATC AATGATTCTT TCTTGGCAAT TTCTGTTTGT TCCAACACAG   400

TTAACACCAA TGGAGTGAAG GATCAGGGTC ATCTTAAAGT TCTTTCTCTT   450

GCCCAATTGC ATCCCTTTGA ACCTGTGATG AGCAGGTCAG AGATTGCTAG   500

CAGATTCCGG CTCCAAGAAG AAGATATAAT TCCTGATGAC AAATATATAT   550

CTGCTGCTAA CAAGGGATCT GTCTCCTGTG TCAAAGAACA TACTTACAAA   600

GTCGAAATGA GCGACAATCA GGGTTTAGGC AAAGTGAATG TTCTTTCTCC   650

TAAGAGAAAT GTTCATGAGT GGCTGTATAG TTTCAAACCA AATTTCAACC   700

AGATCGAAAG TAATAACAGA ACTGTAAATT CTCTTGCAGT CAAATCTTTG   750

CTCATGGCTA CAGAAAACAA CATTATGCCT AACTCTCAAG CTTTTGTTAA   800
```

-continued

```
AGCTTGTACT GATTCTCATT TTAAGTTGAG CCTTTGGCTG AGAATTCCAA      850

AAGTTTTGAA GCAAATAGCC ATACAGAAGC TCTTCAAGTT TGCAGGAGAC      900

GAAACCGGTA AAAGTTTGTA TTTGTCTATT GCATGCATCC CAAATCACAA      950

CAGTGTGGAA ACAGCTTTAA ATGTCACTGT TATATGTAGA CATCAGCTTC     1000

CAATCCCTAA GTCCAAAGCT CCTTTTGAAT TATCAATGAT TTTCTCCGAT     1050

CTGAAAGAGC CTTACAACAC TGTGCATGAT CCTTCATATC CTCAAAGGAT     1100

TGTTCATGCT TTGCTTGAGA CTCACACTTC CTTTGCACAA GTTCTCTGCA     1150

ACAAGCTGCA AGAAGATGTG ATCATATATA CTATAAACAG CCCTGAACTA     1200

ACCCCAGCTA AGCTGGATCT AGGTGAAAGA ACCTTGAACT ACAGTGAAGA     1250

TGCTTCGAAG AAGAAGTATT TTCTTTCAAA AACACTCGAA TGCTTGCCAG     1300

TAAATGTGCA GACTATGTCT TATTTGGATA GCATCCAGAT TCCTTCATGG     1350

AAGATAGACT TGCCAGAGG AGAGATCAGA ATCTCCCTC AATCTACTCC      1400

TATTGCAAGA TCTTTGCTCA AGCTGGATTT GAGCAAGATC AAGGAAAAGA     1450

AGTCCTTGAC TTGGGAAACA TCCAGCTATG ATCTAGAATA AAAGTGGCTC     1500

ATACTACTCT AAGTAGTATT TGTCAACTTG CTTATCCTTT ATGTTGTTTA     1550

TTTCTTTTAA ATCTAAAGTA AGTTAGATTC AAGTAGTTTA GTATGCTATA     1600

GCATTATTAC AAAAAATACA AAAAAATACA AAAAAATACA AAAATATAA      1650

AAAACCCAAA AAGATCCCAA AAGGGACGAT TTGGTTGATT TACTCTGTTT     1700

TAGGCTTATC TAAGCTGCTT TTGTTTGAGC AAAATAACAT TGTAACATGC     1750

AATAACTGGA ATTTAAAGTC CTAAAAGAAG TTTCAAAGGA CAGCTTAGCC     1800

AAAATTGGTT TTTGTTTTTG TTTTTTTGTT TTTTGTTTTT TTGTTTTATT     1850

TTTATTTTTA GTTTATTTTT TGTTTTTGTT ATTTTTATTT TTATTTTATT     1900

TTCTTTTATT TTATTTATAT ATATATCAAA CACAATCCAC ACAAATAATT     1950

TTAATTTCAA ACATTCTACT GATTTAACAC ACTTAGCCTG ACTTTATCAC     2000

ACTTAACACG CTTAGTTAGG CTTTAACACA CTGAACTGAA TTAAAACACA     2050

CTTAGTATTA TGCATCTCTT AATTAACACA CTTTAATAAT ATGCATCTCT     2100

GAATCAGCCT TAAAGAAGCT TTTATGCAAC ACCAGCAATC TTGGCCTCTT     2150

TCTTAACTCC AAACATTTCA TAGAATTTGT CAAGATTATC ACTGTAATAG     2200

TCCATAGCAA TGCTTCCCTT AGCATTGGGA TTGCAAGAAC TAAGTATCTT     2250

GGCATATTCT TTCCCTTTGT TTATCTGTGC ATCATCCATT GTAAATCCTT     2300

TGCTTTTAAG CACTGTGCAA ACCTTCCCCA GAGCTTCCTT AGTGTTGTAC     2350

TTAGTTGGTT CAATCCCTAA CTCCTTGTAC TTTGCATCTT GATATATGGC     2400

AAGAACAACA CTGATCATCT CGAAGCTGTC AACAGAAGCA ATGAGAGGGA     2450

TACTACCTCC AAGCATTATA GCAAGTCTCA CAGATTTTGC ATCTGCCAGA     2500

GGCAGCCCGT AAGCTTGGAC CAAAGGGTGG GAGGCAATTT TGCTTTGAT     2550

AATAGCAAGA TTCTCATTGT TTGCAGTCTC TTCTATGAGC TTCACTCTTA     2600

TCATGCTATC AAGCCTCCTG AAAGTCATAT CCTTAGCTCC AACTCTTTCA     2650

GAATTTTTCT TTATCGTGAC CTTACCAAAA GTAAAATCAC TTTGGTTCAC     2700

AACTTTCATA ATGCCTTGGC GATTCTTCAA GAAAGTCAAA CATGAAGTGA     2750

TACTCATTTT CTTAATCAGG TCAAGATTTT CCTGACAGAA AGTCTTAAAG     2800
```

-continued

```
TTGAATGCGA CCTGGTTCTG GTCTTCTTCA AACTCAACAT CTGCAGATTG    2850

AGTTAAAAGA GAGACAATGT TTTCTTTTGT GAGCTTGACC TTAGACATGG    2900

TGGCAGTTTA GATCTAGACC TTTCTCGAGA GATAAGATTC AAGGTGAGAA    2950

AGTGCAACAC TGTAGACCGC GGTCGTTACT TATCCTGTTA ATGTGATGAT    3000

TTGTATTGCT GAGTATTAGG TTTTTGAATA AAATTGACAC AATTGCTCT     3049
```

The deduced amino acid sequences of the nonstructural (single underlined above) and nucleocapsid proteins according to the present invention are (SEQ. ID. No.12).

```
Met Ser Ser Gly Val Tyr Glu Ser Ile Ile Gln Thr Lys Ala Ser Val
1               5                   10                  15

Trp Gly Ser Thr Ala Ser Gly Lys Ser Ile Val Asp Ser Tyr Trp Ile
                20                  25                  30

Tyr Glu Phe Pro Thr Gly Ser Pro Leu Val Gln Thr Gln Leu Tyr Ser
            35                  40                  45

Asp Ser Arg Ser Lys Ser Ser Phe Gly Tyr Thr Ser Lys Ile Gly Asp
        50                  55                  60

Ile Pro Ala Val Glu Glu Ile Leu Ser Gln Asn Val His Ile Pro
65                  70                  75                  80

Val Phe Asp Asp Ile Asp Phe Ser Ile Asn Ile Asn Asp Ser Phe Leu
                85                  90

Ala Ile Ser Val Cys Ser Asn Thr Val Asn Thr Asn Gly Val Lys His
                100                 105                 110

Gln Gly His Leu Lys Val Leu Ser Leu Ala Gln Leu His Pro Phe Glu
            115                 120                 125

Pro Val Met Ser Arg Ser Glu Ile Ala Ser Arg Phe Arg Leu Gln Glu
        130                 135                 140

Glu Asp Ile Ile Pro Asp Asp Lys Tyr Ile Ser Ala Ala Asn Lys Gly
145                 150                 155                 160

Ser Leu Ser Cys Val Lys Glu His Thr Tyr Lys Val Glu Met Ser His
                165                 170                 175

Asn Gln Ala Leu Gly Lys Val Asn Val Leu Ser Pro Asn Arg Asn Val
            180                 185                 190

His Glu Trp Leu Tyr Ser Phe Lys Pro Asn Phe Asn Gln Ile Glu Ser
        195                 200                 205

Asn Asn Arg Thr Val Asn Ser Leu Ala Val Lys Ser Leu Leu Met Ala
    210                 215                 220

Thr Glu Asn Asn Ile Met Pro Asn Ser Gln Ala Phe Val Lys Ala Ser
225                 230                 235                 240

Thr Asp Ser His Phe Lys Leu Ser Leu Trp Leu Arg Ile Pro Lys Val
                245                 250                 255

Leu Lys Gln Ile Ala Ile Gln Lys Leu Phe Lys Phe Ala Gly Asp Glu
            260                 265                 270

Thr Gly Lys Ser Phe Tyr Leu Ser Ile Ala Cys Ile Pro Asn His Asn
        275                 280                 285

Ser Val Glu Thr Ala Leu Asn Val Thr Val Ile Cys Arg His Gln Leu
    290                 295                 300

Pro Ile Pro Lys Ser Lys Ala Pro Phe Glu Leu Ser Met Ile Phe Ser
305                 310                 315                 320

Asp Leu Lys Glu Pro Tyr Asn Thr Val His Asp Pro Ser Tyr Pro Gln
                325                 330                 335
```

-continued

```
Arg Ile Val His Ala Leu Leu Glu Thr His Thr Ser Phe Ala Gln Val
            340                 345                 350

Leu Cys Asn Lys Leu Gln Glu Asp Val Ile Ile Tyr Thr Ile Asn Ser
            355                 360                 365

Pro Glu Leu Thr Pro Ala Lys Leu Asp Leu Gly Glu Arg Thr Leu Asn
            370                 375                 380

Tyr Ser Glu Asp Ala Ser Lys Lys Lys Tyr Phe Leu Ser Lys Thr Leu
365                 390                 395                 400

Glu Cys Leu Pro Val Asn Val Gln Thr Met Ser Tyr Leu Asp Ser Ile
            405                 410                 415

Gln Ile Pro Ser Trp Lys Ile Asp Phe Ala Arg Gly Glu Ile Arg Ile
            420                 425                 430

Ser Pro Gln Ser Thr Pro Ile Ala Arg Ser Leu Leu Lys Leu Asp Leu
            435                 440                 445

Ser Lys Ile Lys Glu Lys Lys Ser Leu Thr Trp Glu Thr Ser Ser Tyr
            450                 455                 460

Asp Leu Glu
465

Met Ser Lys Val Lys Leu Thr Lys Glu Asn Ile Val Ser Leu Leu
              5                  10                  15

Thr Gln Ser Ala Asp Val Glu Phe Glu Glu Asp Gln Asn Gln Val
             20                  25                  30

Ala Phe Asn Phe Lys Thr Phe Cys Gln Glu Asn Leu Asp Leu Ile
             35                  40                  45

Lys Lys Met Ser Ile Thr Ser Cys Leu Thr Phe Leu Lys Asn Arg
             50                  55                  60

Gln Gly Ile Met Lys Val Val Asn Gln Ser Asp Phe Thr Phe Gly
             65                  70                  75

Lys Val Thr Ile Lys Lys Asn Ser Glu Arg Val Gly Ala Lys Asp
             80                  85                  90

Met Thr Phe Arg Arg Leu Asp Ser Met Ile Arg Val Lys Leu Ile
             95                 100                 105

Glu Glu Thr Ala Asn Asn Glu Asn Leu Ala Ile Ile Lys Ala Lys
            110                 115                 120

Ile Ala Ser His Pro Leu Val Gln Ala Tyr Gly Leu Pro Leu Ala
            125                 130                 135

Asp Ala Lys Ser Val Arg Leu Ala Ile Met Leu Gly Gly Ser Ile
            140                 145                 150

Pro Leu Ile Ala Ser Val Asp Ser Phe Glu Met Ile Ser Val Val
            155                 160                 165

Leu Ala Ile Tyr Gln Asp Ala Lys Tyr Lys Glu Leu Gly Ile Glu
            170                 175                 180

Pro Thr Lys Tyr Asn Thr Lys Glu Ala Leu Gly Lys Val Cys Thr
            185                 190                 195

Val Leu Lys Ser Lys Gly Phe Thr Met Asp Asp Ala Gln Ile Asn
            200                 205                 210

Lys Gly Lys Glu Tyr Ala Lys Ile Leu Ser Ser Cys Asn Pro Asn
            215                 220                 225

Ala Lys Gly Ser Ile Ala Met Asp Tyr Tyr Ser Asp Asn Leu Asp
            230                 235                 240
```

```
Lys Phe Tyr Glu Met Phe Gly Val Lys Lys Glu Ala Lys Ile Ala
                245             250             255
Gly Val Ala
```

As the nucleocapsid protein gene depicted above is on the viral complementary strand, the nucleocapsid protein gene of TSWV-B is (SEQ. ID. No.15).

```
TTATGCAACA CCAGCAATCT TGGCCTCTTT CTTAACTCCA AACATTTCAT AGAATTTGTC   60
AAGATTATCA CTGTAATAGT CCATAGCAAT GCTTCCCTTA GCATTGGGAT TGCAAGAACT  120
AAGTATCTTG GCATATTCTT TCCCTTTGTT TATCTGTGCA TCATCCATTG TAAATCCTTT  180
GCTTTTAAGC ACTGTGCAAA CCTTCCCCAG AGCTTCCTTA GTGTTGTACT TAGTTGGTTC  240
AATCCCTAAC TCCTTGTACT TTGCATCTTG ATATATGGCA AGAACAACAC TGATCATCTC  300
GAAGCTGTCA ACAGAAGCAA TGAGAGGGAT ACTACCTCCA AGCATTATAG CAAGTCTCAC  360
AGATTTTGCA TCTGCCAGAG GCAGCCCGTA AGCTTGGACC AAAGGGTGGG AGGCAATTTT  420
TGCTTTGATA ATAGCAAGAT TCTCATTGTT TGCAGTCTCT TCTATGAGCT TCACTCTTAT  480
CATGCTATCA AGCCTCCTGA AAGTCATATC CTTAGCTCCA ACTCTTTCAG AATTTTTCTT  540
TATCGTGACC TTACCAAAAG TAAAATCACT TTGGTTCACA ACTTTCATAA TGCCTTGGCG  600
ATTCTTCAAG AAAGTCAAAC ATGAAGTGAT ACTCATTTTC TTAATCAGGT CAAGATTTTC  660
CTGACAGAAA GTCTTAAAGT TGAATGCGAC CTGGTTCTGG TCTTCTTCAA ACTCAACATC  720
TGCAGATTGA GTTAAAAGAG AGACAATGTT TTCTTTTGTG AGCTTGACCT TAGACAT     777
```

The complementary nucleic acid molecule has a nucleotide sequence as shown in SEQ. ID. No. 19.

The compete S RNA of TSWV-B should be 3049 nucleotides in length, 134 nucleotides longer than S RNA of TSWV-CPNH1. This difference was mainly attributed to the elongated intergenic region of the TSWV-B S RNA. Analysis of the sequenced region of TSWV-B S RNA revealed two open reading frames as depicted above, which is similar to other TSWV isolates. The larger one was localized on the viral RNA strand originating at nucleotide 88 and terminating at nucleotide 1491. The smaller one of the viral complementary strand was defined by an initiation codon at nucleotide 2898 and a termination codon at nucleotide 2122. The two open reading frames were separated by an intergenic region of 629 nucleotides. Comparisons of the entire sequenced TSWV-B S RNA with S RNA with S RNA regions of other isolates in the following table which depicts the percent homology comparison of aligned nucleotide and amino acid sequences of the TSWV-B S RNA with those of the other isolates:

| Comparisons[a] | Overall nt | 53 K protein gene | | Intergenic nt | 29 K protein gene | |
|---|---|---|---|---|---|---|
| | | nt | aa | | nt | aa |
| B/CPNH1 | 76.4[b] | 80.0 | 86.1(78.3)[c] | 72.4 | 77.5 | 91.5(79.1) |
| B/L3 | 75.8 | 79.0 | 89.0(82.0) | 76.4 | 78.0 | 91.1(79.9) |
| B/BL | 76.3 | — | — | 72.8 | 77.6 | 90.3(79.5) |
| B/I | 63.0 | — | — | — | 63.1 | 69.7(55.3) |
| CPNH1/L3 | 94.8 | 95.6 | 92.0(89.4) | 89.2 | 96.8 | 99.6(98.5) |
| CPNH1/BL | 96.4 | — | — | 95.9 | 97.2 | 98.8(96.9) |
| CPNH1/I | 62.7 | — | — | — | 60.8 | 69.5(55.1) |
| L3/BL | 95.1 | — | — | 92.6 | 97.3 | 99.2(98.5) |
| L3/I | 60.9 | — | — | — | 60.9 | 69.5(55.1) |
| I/BL | 61.7 | — | — | — | 60.9 | 68.8(53.9) |

[a]The partial or complete S RNA sequences of isolates TSWV-CPNH1 (2.916 kb), TSWV-L3 (2.837 kb), TSWV-BL (2.037 kb) and TSWV-1 (1.144 kb) were used for comparisons with the S RNA sequence of the TSWV-B (3.049 kb).
[b]Percent similarities were calculated by Comparison of their nucleotide or predicted amino acid sequence using the program BESTFIT of the GCG Sequence analysis software package.
[c]Percent identity is in parenthesis.

As depicted, the greatest nucleotide sequence similarity (75.8%–76.4%) was shown with the L-type isolates (CHNH1, L3 and BL). To the lesser extent, there was nucleotide sequence similarity (63%) between the TSWV-B S RNA and the S RNA of TSWV-I assigned to I serogroup. For comparison, the sequenced S RNA regions of the L-type isolates (CHPN1, L3 and BL) shared 94.8%–96.4% nucleotide sequence similarities.

The open reading frame of 777 nucleotides encodes the N protein of 258 amino acids with a predicted molecular weight of 28700 Da. The sequence comparisons of the N open reading frame from TSWV isolates revealed that nucleotide sequences of the N genes from the isolates CPNH1, L3 and BL differ from TSWV-B by a considerably larger amount (22%–22.5%) than they differ from each other (2.7%–3.2%). Consistent to the results of the immunological analysis, the N amino acid sequences among CPNH1, L3 and BL isolates are more closely related to each other (98.8%–99.6% similarities or 96.9%–98.5% identities) than to the TSWV-B (90.3%–91.5% similarities or 79.1%–79.9% identities). Much lower homology was observed to TSWV-I at both nucleotide (63.1%) and amino acid (69.7% similarity or 55.3% identity) levels. Except for the N open reading frame of TSWV-I that encodes 262 amino acids, the N open reading frames of the other isolates code for the 258 amino acids. Computer analysis suggested that the extra residues of TSWV-I N open reading frame resulted from the amino acid sequence insertions (residues 82 through 84 and residue 116). One potential N-glycosylation site is found at residue 68.

The second open reading frame of 1404 nucleotides encodes the nonstructural protein of 467 amino acids with a predicted molecular weight of 52566 Da. Comparisons with homologous open reading frames of TSWV-CPNH1 and TSWV-L3 showed 80% and 79% similarities at the nucleotide level, and 86.1% (or 78.3% identity) and 89% (or 82.0% identity) similarities at the amino acid level. This open reading frame contains four potential glycosylation sites, which are located in the exact same position as those of TSWV-CPNH1 and TSWV-L3.

The intergenic region of the TSWV-B S RNA was, due to several insertions, 126 and 41 nucleotide longer than the counterparts of TSWV-CPNH1 and TSWV-L3, respectively. The sequence analysis by the program FOLD indicated the intergenic region can form very complex and stable hairpin structure by internally base-pairing U-rich stretches with A-rich stretches of the intergenic region, which had similar stability to those produced from TSWV-CPNH1 and TSWV-L3 as indicated by minimum free energy values. This internal base-paired structure may act as a transcription termination signal.

The results tabulated above also revealed that the N protein of TSWV-B is subject to a higher degree of selective pressure than the 52 K protein; the similarities among the amino acid sequences of the 52 K protein are lower than that found for the amino acid sequence of the NPs. Nucleotide sequence divergence is highest among the intergenic regions, which indicates that this region is subject to less selective pressure than either genetic region.

The evolutionary relationships among the TSWV-B and other four TSWV isolates were analyzed and depicted in FIG. 4 in which the evolutionary tree organization is consistent with the relatedness of serological data collected for these TSWV isolates. Thus, the TSWV-B, according to the present invention, is more closely related to the L-type isolates than to the I-type isolate TSWV-I, but is much less similar to the L-type isolates than the L-type isolates are to each other.

Despite a slight delay of symptom expression, transgenic plants did not show resistance to the Brazil isolate of TSWV; Serological results show that this isolate is distinct from the "L" and "I" type isolates, and biologically different from the circurbit isolate. The Brazil isolate may thus belong to still another serogroup of TSWV. In any event, infectivity results show that it is unlikely that a single NP gene will provide resistance to all isolates in the Tospovirus genus.

Transgenic plants according to the present invention that gave low or undetectable ELISA reactions (0–0.05 $OD_{405\ nm}$) were resistant to infection by the heterologous isolates (Arkansas and 10W pakchoy) of the "L" serogroup, whereas no protection against these isolates was found in plants accumulating high levels of the NP. Compared to the ELISA readings of control NP(–) plants (0.05 $OD_{405\ nm}$), these transgenic plants may produce little, if any, TSWV-BL NP. Similar results have been observed in transgenic plants, in which the CP accumulation was not detected; these were highly resistant to virus infection. The mechanism underlying this phenomenon is presently unknown. It is likely that this type of resistance might be attributed to interference of CP RNA molecules produced in transgenic plants with viral replication, presumably by hybridizing to minus-sense replicating RNA of the attacking virus, binding to essential host factors (e.g., replicase) or interfering with virion assembly.

It should be noted, however, that the resistance to the homologous TSWV-BL isolate is apparently independent of the expression levels of the NP gene. Although the relative NP levels of the individual $R_1$ plants inoculated with TSWV-BL were not measured, it is reasonable to assume that the NP produced in these inoculated $R_1$ plants (a total of 145 plants tested) ranged from undetectable to high.

In contrast to the case for protection against the heterologous isolates of the "L" serogroup, protection against the Begonia isolate of the TSWV-I serogroup was found in the high NP-expressing $R_1$ plants. Comparison of NP nucleotide sequence of the "L" serogroup with that of the "I" serogroup revealed 62% and 67% identity at the nucleotide and amino acid levels, respectively. The difference of NP genes of the two serogroups might be so great that the NP (the "L" serogroup) produced in transgenic plants acted as a dysfunctional protein on the attacking Begonia isolate of the "I" serogroup. Incorporation of this "defective" coat protein into virions may generate defective virus which inhibit virus movement or its further replication. This type of interaction is expected to require high levels of the NP for the protection. Alternatively, resistance to the Begonia isolate may also involve interference of NP transcripts produced in $R_1$ plants with viral replication. If this is true, more NP transcripts (due to the heterologous nature of two NP gene) may be required to inhibit replication of heterologous virus.

Although there are no obvious explanations for the results showing the relation of NP levels in individual $R_1$ plants to resistance to the heterologous isolates of the "L" and "I" serogroups, it is believed these are definite trends since the data were derived from a large number (190) of plants. Thus, it is believed that a measurement of CP or NP levels in individual plants may provide a more accurate way to relate NP or CP levels to resistance. By this form of data analysis, the results show that the resistance was more closely related to NP levels in each test plant than to the NP level of the $R_0$ line from which they were derived. For TSWV-BL Np gene in tobacco, at least, it appears that integration sites of the NP gene in plant chromosome may not be important for viral resistance.

Studies have also been conducted to determine the reaction of transgenic $R_1$ and $R_2$ tomatoes containing the nucleocapsid protein gene of TSWV-BL according to the present invention to the following isolates: Brazil (a distantly related virus), T91 ( a closely related virus) and BL (a homologous isolate). In these studies, transgenic tomatoes (*L. esculentum*) were produced by *A. tumefaciens*-mediated gene transfer of the nucleocapsid protein (N) gene of the lettuce isolate of tomato spotted with virus BL into germinated cotyledons using modifications of published procedures [see Plant Cell Reports 5:81 (1986)]. The tomato line "Geneva 80" was selected for transformation because it contains the Tm-22 gene which imparts resistance to TMV, thus creating the possibility of producing a multiple virus-resistant line.

Transformants were selected on kanamycin media and rooted transgenic tomatoes were potted and transferred into the greenhouse. $R_1$ and $R_2$ tomato seedlings expressed the NPT II gene, suggesting multiple insertions of this gene in the plant genome. In contrast, only 18% of the seedlings produced detectable levels of the N protein.

Nine $R_1$ and three $R_2$ lines were tested for resistance to the following three Tospovirus described, specifically TSWV-BL, TSWV-T91, and TSWV-B. Infectivity was based upon visual inspection of test plants. In those cases where plants appeared healthy except for a few rust-colored rings or insect damage, extracts from these plants were inoculated to *N. benthamiana* to test for the presence of the virus. As depicted in the following table, nearly all control tomato plants exhibited typical symptoms consisting of plant stunting, leaf yellow mosaic and rugosity 3 to 4 weeks after inoculations with TSWV-BL, TSWV-T91 or TSWV-B. However, only 4% of the $R_1$ and $R_2$ transgenic plants became infected with TSWV-BL, 7% with TSWV-T91, and 45% with TSWV-B.

Viral resistance in transgenic R1 and R2 tomatoes expressing the nucleoprotein gene of the lettuce strain of tomato spotted wilt virus

| | Inoculating Isolates[a] | | |
|---|---|---|---|
| Plant Line | TSWV-BL | TSWV-T91 | TSWV-B |
| R1 Plants: | | | |
| T13-1 | 0/22 | 1/26 | 7/24 |
| T13-2 | 6/20 | NT[b] | NT |
| T13-3 | 2/42 | 0/20 | 12/18 |
| T13-4 | 0/25 | NT | NT |
| T13-9 | 0/20 | NT | NT |
| T13-10 | 1/50 | 2/26 | 11/26 |
| T13-11 | 0/22 | NT | NT |
| T13-12 | 1/29 | NT | NT |
| T13-13 | 0/22 | NT | NT |
| TOTAL | 10/252 | 3/72 | 30/68 |
| R2 Plants: | | | |
| T13-1-7 | 0/8 | 2/8 | 5/8 |
| T13-1-9 | 0/8 | 1/8 | 2/8 |
| T13-1-11 | 0/8 | 1/9 | 5/9 |
| TOTAL | 0/24 | 4/25 | 12/25 |
| CONTROLS | 92/95 | 51/53 | 52/53 |

[a]plants were inoculated at the one- to two-leaf stage with 5-, 10-, or 20-fold diluted leaf extract of *N. benthamiana*, H423 tobacco or tomato; the same plants were re-inoculated 7 days later and symptoms were recorded after another 14 days; the reaction is expressed as number of plants with symptoms/number of plants tested
[b]not tested Accordingly, the description above supports the finding that transgenic tomato plants that express the N gene of TSWV-BL show resistance to infection to TSWV-BL, to other TSWV isolates that are closely related to TSWV-BL, and to the more distantly related TSWV-B.

In further limited studies with an additional isolate, all transgenic plants were resistant to the 10W (pakchoy) isolate, whereas the controls were infected. These results show that transgenic tomatoes are better protected against closely related isolates than distantly related isolates. Unlike in transgenic tobacco and *N. benthamiana* expressing the TSWV-BL N gene, the level of N protein expression did not correlate with the observed protection in transgenic tomatoes; 55% of the transgenic tomatoes were also resistant to a distantly related isolate of TSWV-B, which was not observed in transgenic tobacco and *N. benthamiana* plants. These discrepancies may reflect that tomato is inherently less susceptible to Tospoviruses.

In addition, studies were also conducted to determine virus distribution in a small number of plants at 5 and 7 weeks after inoculation. The distal halves from leaflets of all expanded leaves of each plant were ground and back-inoculated onto *N. benthamiana.* The results taken seven days after inoculation showed that virus cannot be recovered from any leaf tissue of asymptomatic transgenic plants inoculated with either TSWV-BL. -T91, or -B, confirming the visual findings reported above. In transgenic plants showing symptoms, the virus is not distributed throughout the plant. For example, a transgenic plant which could not be conclusively rated visually contained the virus in only two of the 8 leaves; the second leaves from the bottom and top of the plant. Conversely, virus was present in all leaves of the infected control plant and was absent in those of the healthy control plants.

Graft inoculations were attempted to test whether the resistant transgenic plants could become infected if virus is introduced into the vascular system. $R_1$ and $R_2$ plants that had been inoculated at 1:5, 1:10 or 1:20 daltons of TSWV-BL, -T91, or -B were grafted onto control plants infected with the same isolates and dilutions. The 34 transgenic plants were asymptomatic after 31 days, although the non-transgenic controls were infected. After 23 days, the top 46 cm of transgenic plants had been trimmed away to induce new growth and more plant stress. Although the young, vigorously growing new shoots failed to show any symptoms on the 31st day post inoculation, 33%, 31% and 45% of TSWV-BL, -T91 and -B were showing leaf or stem symptoms, respectively at 45 days post inoculation. These results indicate that some transgenic plants are tolerant, and others are immune to infection.

Thus, according to one aspect of the present invention, transgenic plants expressing the NP gene of the TSWV-BL isolate are highly resistant to infections of both the homologous TSWV-BL isolate and heterologous isolates of the same serogroup (Arkansas and 10W pakchoy). More significantly, the resistance is effective to Begonia isolate from other serogroups. In brief, the above clearly describes that transgenic tobacco plants expressing the nucleoprotein gene of TSWV-BL display resistance to both TSWV and INSV, and the protection appears to be mediated by the nucleoprotein against distantly related INSV and by the nucleoprotein gene ribonucleotide sequence against the homologous and closely related TSWV isolates. This is the first time broad spectrum resistance of the engineered plants to different isolates of TSWV has been shown.

While coat protein protection generally displays delay and/or reduction in infection and symptom expression, but no immunity, the present invention provided a significantly high percentage of transgenic plants which were symptom-free and free of the infective virus. Resistance of these plants under greenhouse conditions persisted throughout their life cycle, and more importantly was inherited to their progenies as shown above.

It was observed in the present invention that the transgenic plants producing little, if any, TWSV-BL NP were highly resistant to infection by the homologous isolate and other closely-related isolates within the same serogroup of TSWV, whereas no protection was found in those expressing high levels of the NP gene.

The biological diversity of TSWV is well documented and has been reported to overcome the genetic resistance in cultivated plants such as tomato. Thus, it is extremely important to develop transgenic plants that show resistance to many strains of TSWV. The present invention indicates that one method to do so would be to utilize the viral NP gene to confer this resistance, and that this resistance would be to diverse TSWV isolates. Thus, the finding of the present invention that the expression of TSWV NP gene is capable of conferring high levels of resistance to various TSWV isolates has a great deal of commercial importance.

In another series of studies, Plasmid BIN19-N$^+$ was constructed and transferred to *A. tumefaciens* strain LBA4404 in accordance with Example IV, and transferred to *Nicotiana benthamiana* in accordance with Example V. The nucleocapsid genes of INSV-Beg and -LI were amplified with oligomer primers INSV-A (5'-TAGTTATCTAGAACCATGGACAAAGCAAAGATTA CCAAGG) (SEQ ID NO. 20) and INSV-B (5'-TAGAGTGGATCCATGGTTATTTCAAATAATTTATA AAAGCAC) (SEQ ID NO. 21), hybridizing to the 5'-coding and 3'-noncoding regions of the nucleocapsid gene of an INSV isolate, respectively. The amplified nucleocapsid gene fragments were purified in accordance with Example III, and digested and sequenced in accordance with Example IV.

Of a total of 24 N+ (transformed with pBIN19-N$^+$) and 18 N$^-$ (transformed with vector pBIN19) transgenic *N. benthamiana* plants that were transferred to soil and grown in the greenhouse, all N$^+$ lines were confirmed by PCR at leaf stages 4–5 to contain the N gene sequence. The relative level of N protein accumulation was estimated in each independent $R_0$ transgenic clonal line by DAS-ELISA using antibodies of the TSWV-BL N protein. Of the twenty-four N$^+$ lines, two had $OD_{405\ nm}$ readings of 0.50–1.00, seventeen between 0.02–0.10, and the remaining five less than 0.02. Healthy *N. benthamiana* or transgenic N$^-$ plants gave $OD_{405\ nm}$ readings of 0.00–0/02. All the $R_0$ plants were self-pollinated and the seeds from the following transgenic lines were germinated on kanamycin (300 μg/ml) selection medium for inoculation tests: (1) N$^-$-2 and -6, control transgenic lines containing vector pBIN19 alone; (2) N$^+$-28, a transgenic line that produced an undetectable amount of the N protein (OD405 nm=0.005); (3) N$^+$-21, a transgenic line producing a low level of the N protein (OD405 nm=0.085); and (4) N$^+$-34 and -37, two transgenic lines accumulating high levels of the N protein (OD405 nm=0.50–1.00. These six lines were then analyzed by Northern hybridization; the intensity of N gene transcripts correlated well with the levels of ELISA reactions.

Transgenic seedlings from the six $R_0$ lines were selected by germinating seeds on kanamycin selection medium, and these seedlings were inoculated with the five Tospoviruses. The inoculated R1 plants were rated susceptible if virus symptoms were observed on uninoculated leaves. In order to exclude the possibilities of escapes, transgenic control N$^-$ plants were always used in each inoculation of transgenic N$^+$ plants. In addition, each inoculum extract was always used to first inoculate N$^+$ plants followed by control N$^-$ plants. The results from this series of studies are depicted below:

Reactions of $R_1$ plants expressing the nucleocapsid (N) protein gene of *N. benthamiana* spotted wilt virus (TSWV) to inoculation with Tospoviruses

| | | No. plants infected/No. plants inoculated[b] | | | | |
|---|---|---|---|---|---|---|
| | | TSWV ISOLATE | | INSV ISOLATE | | |
| R0 Line | ELISA[a] | BL | 10W | Beg | L1 | TSWV-B |
| N--2/-6 | <0.02 | 32/32 | 32/32 | 32/32 | 20/20 | 32/32 |
| N+-28 | 0.005 | 16/16 | 16/16 | 15/16 | | 16/16 |
| N+-21 | 0.085 | 9/40 | 17/40 | 39/40 | 18/20 | 40/40 |
| N+-34 | 0.715 | 25/28[c] | 28/28 | 23/28[c] | | 28/28 |
| N+-37 | 0.510 | 26/28[c] | 22/22 | 21/28[c] | 16/20[c] | 22/22 |

[a]ELISA data of $R_0$ lines from which the $R_1$ plants were derived;
[b]30-fold diluted leaf extracts of infected *N. benthamiana* plants were applied to the three leaves of plants at the 3–5 leaf stages. Each extract was always used to inoculate N+ plants followed by control N– plants. Data were taken daily for at least two months after inoculation and expressed as number of plants systemically infected/number of plants inoculated;
[c]indicate that nearly all susceptible R1 plants displayed a significant delay of symptom appearance.

As depicted in the above table, all R1 plants from control lines N$^-$-2 and -6 showed systemic symptoms 5–8 days after inoculation with all the viruses tested. None of the $R_1$ plants from line N$^+$-28 produced detectable levels of the N protein, and all were susceptible to these viruses except for one plant inoculated with INSV-Beg. ELISA assays of leaf discs from this N$^+$-28 $R_1$ plant sampled before inoculation clearly showed that the plant identified to possess the INSV-Beg resistant phenotype did accumulate a high level of the N protein (OD405 nm=0.78 as compared to $OD4_{05\ nm}$<0.02 for all other N$^+$-28 $R_1$ plants).

The low N gene expressing line N$^+$-21 showed the best resistance against the homologous (78%) and closely related TSWV-10W (57%) isolates the very little resistance to the low INSV isolates (3% and 10%); and only three N$^+$-21 plants showed the resistant phenotype when inoculated with the INSV isolates. Leaf samples from these INSV-resistant N$^+$-21 $R_1$ plants gave much higher ELISA reactions ($OD_{405\ nm}$ 0.5 to 1.00) and thus higher amounts of the N protein than the susceptible N$^+$-21 plants ($OD_{405\ nm}$ 0.02 to 0.20). The high N gene expressing lines N$^+$-34 and -37 showed the highest resistance to INSV isolates (18%–25%) followed by the homologous TSWV-BL isolate (7% and 11%) while none of the plants showed resistance to TSWV-10W; however, the N$^+$-34 and -37 $R_1$ plants that became infected with INSV or TSWV-BL did show various lengths of delays in symptom expression. None of the R1 plants from these four transgenic N$^+$ lines were resistant to TSWV-B; some of the R1 plants from the N$^+$-34 and -37 lines showed a slight delay of symptom appearance.

In studies to determine whether the level of N protein production in N$^+$ $R_1$ plants was associated with resistance to different Tospoviruses, the inoculated N$^+$ $R_1$ plants in the preceding table were re-organized into four groups based on the intensity of their ELISA reactions of tissues taken before inoculation irrespective of original $R_0$ plants. The N$^+$ $R_1$ plants that expressed low levels of the N protein (0.02–0.2 OD) showed high resistance (100% and 80%) to TSWV-BL and -10W but were all susceptible to INSV-Beg and -LI, showing no detectable delay in symptom expression relative to control N$^-$ plants. In contrast, nearly all N$^+$ $R_1$ plants with high levels of the N protein (0.20–1.00 OD) showed various levels of protection against TSWV-BL, INSV-Beg and -LI, ranging from a short delay of symptom expression to complete resistance with most of these plants showing various lengths of delay in symptom development relative to control N⁻ plants. No protection was observed in the high expressors against TSWV-10W. In addition, none of the N⁺ $R_1$ plants were resistant to TSWV-B regardless of the level of N gene expression; however, a short delayed symptom appearance was observed in the N⁺ $R_1$ plants producing high levels of the N protein. All control N⁻ $R_1$ plants and transgenic N⁺ $R_1$ plants with undetectable ELISA reactions (0 to 0.02 OD) were susceptible to all the Tospoviruses tested.

The inhibition of replication of a distantly related INSV in *N. benthamiana* protoplasts expressing the TSWV-BL nucleocapsid gene was also studied. In these studies, whole INSV-LI virions were used to infect protoplasts that were isolated from three transgenic lines to investigate how the products of the transgene affect replication of the incoming virus. Viral replication was determined by measuring the level of the N protein of the infecting INSV in transgenic protoplasts using antibodies specific to the INSV N protein. DAS-ELISA analysis showed that all progenies from a given line were relatively uniform and nearly all $R_1$ progeny gave an expression level of transgenic N gene similar to their parental transgenic line. These results allowed for the prediction of the expression level of $R_1$ populations based on that of their parental lines. Protoplasts derived from $R_1$ plants of the low expressor line N⁺-21 supported the replication of INSV-LI whereas protoplasts from $R_1$ plants of the higher expressor line N⁺-37 did not until 42 hours after inoculation at which low levels of viral replication were observed. The same protoplasts at various time intervals (e.g. 0, 19, 30 and 42 hours) were also assayed by DAS-ELISA using antibodies specific to the TSWV-BL N protein to monitor the expression level of the transgene. As expected, protoplast from N⁺-21 $R_1$ plants produced relatively low levels (0.338–0.395 OD405 nm) whereas protoplasts from N⁺-37 $R_1$ plants accumulated high levels (0.822–0.865 $OD_{405}$ nm). The expression level was found to be consistent at all time points.

In this aspect of the present invention it has been shown that transgenic *N. benthamiana* plants that accumulate low amounts of the TSWV-BL N protein are highly resistant to the homologous and closely related (TSWV-10W) isolates, while plants that accumulate high amounts of this protein posses moderate levels of protection against both the homologous and distantly related (INSV-Beg and INSV-LI) viruses. More importantly, these findings indicate that transgenic *N. benthamiana* plants (a systemic host of INSV) are protected against INSV-Beg and INSV-LI isolates.

As discussed above, we have shown that transgenic plants expressing the N gene of TSWV are resistant to homologous isolates, and that such plants expressing the TSWV-BL N gene are resistant to both TSWV and INSV. It has also been shown the best resistance to homologous and closely related isolates was found in transgenic plants accumulating low levels of N protein while transgenic plants with high levels of TSWV-BL N protein were more resistant to serologically distant INSV isolates. This observation led us to suspect the role of the translated N protein product in the observed protection against homologous and closely related isolates and to speculate that either the N gene itself which was inserted into the plant genome or its transcript was involved in the protection. To test this hypothesis transgenic plants containing the promoterless N gene or expressing the sense or antisense untranslatable N coding sequence were produced. What was discovered was that both sense and antisense untranslatable N gene RNAs provided protection against homologous and closely related isolates, and that these RNA-mediated protections were most effective in plants that synthesized low levels of the respective RNA species and appears to be achieved through the inhibition of viral replication.

More specifically, the coding sequences introduced into transgenic plants is shown in FIG. 7. As depicted, the construct pBIN19-N contains the promoterless N gene inserted into the plant transformation vector pBIN19 (see Example IV). All other constructs contain a double 35S promoter of CaMV, a 5'-untranslated leader sequence of alfalfa mosaic virus and a 3'-untranslated/polyadenylation sequence of the nopaline synthase gene. pBI525 is a plant expression vector and is used in this study as a control; pIB525-mN contains the mutant (untranslatable) form of the N gene; pBI525-asN contains the antisense form of the untranslatable N gene. One nucleotide deletion at the 5'-terminus of the mutant N gene is indicated by the dash symbol. ATG codons are underlined and inframe termination codons in the mutant gene are shown in bold.

EXAMPLE VIII

Primer-directed mutagenesis and cloning of the TSWV-BL N gene was conducted as follows Full-length N gene was obtained by reverse transcription and polymerase chain reaction as described in Phytopathology 82:1223 (1992), the disclosure of which is incorporated in toto herein. The untranslatable N coding sequence was similarly generated by RT-PCR using oligomer primers A (AGCATTGGATCCATGGTTAACACACTAAGCAAGC AC) (SEQ ID NO. 22), which is identical to the S RNA in the 3'-noncoding region of the TSWV-BL N gene and B (AGCTAATCTAGAACCATGGATGACTCACTAAGG AAAGCATTGTTGC) (SEQ ID NO. 23), complementary to the S RNA in the 5'-terminus of the N gene. The latter oligomer primer contains a frameshift mutation immediately after the translation initiation codon and several termination codons to block possible translation readthroughs. The intact and mutant N gene fragments were purified on a 1.2% agarose gel as described in Example II. The gel-isolated intact and mutant N gene fragments were digested with the appropriate restriction enzyme(s) and directly cloned into BamHI/XbaI-digested plant transformation vector pBIN19 and NcoI-digested plant expression vector pBI515, respectively as described in Example IV. The resulting plasmids were identified and designated as pBIN19-N containing the intact, promoterless N gene, and pBI525-mN and pB525-asN containing the mutant coding sequence in the sense and antisense orientations, respectively, relative to cauliflower mosaic virus 35S promoter. The translatability of the mutant N coding sequence in the expression cassette was checked by transient expression assay in *Nicotiana tabacum* protoplasts; and the expression cassettes containing the sense or antisense mutant N coding sequence were then excised from plasmid pBI525 by a partial digestion with HindIII/EcoRI (since the N coding sequence contains Internal HindIII and ExoRI sites), and ligated into the plant transformation vector pBIN19 that had been cut with the same enzymes. The resulting vectors as well as pBIN19-N were transferred to *A. tumefaciens* strain LBA4404 using the procedure described in Example IV. Leaf discs of *N. tabacum* var Havana cv 423 were inoculated with the *A. tumefaciens* strain LBA4404 containing various constructs and the resulting transgenic plants were self-pollinated and seeds were selectively germinated on kanamycin medium.

PCR was performed on each $R_0$ transgenic line as described above. The oligomer primers A and B were used to determine the presence of the N coding sequence of TSWV-BL. The oligomer primer 35S-promoter (CCCACTATCCTTCGCAAGACCC) (SEQ ID NO. 24) was combined with either the oligomer primer A to B to confirm the orientation (relative to the CaMV 35S promoter) of the mutant N coding sequence inserted into the plant genome. DAS-ELISA used to detect the N protein in transgenic plants were performed using polyclonal antibodies against the TSWV-BL N protein. For an estimation of RNA transcript level in transgenic plants by Northern blot, total plant RNAs were isolated according to Napoli [see The Plant Cell 2:279 (1990)], and were separated on a formaldehyde-containing agarose gel (10 μg/lane). The agarose gels were then stained with ethidium bromide to ensure uniformality of total plant RNAs in each lane. Hybridization conditions were as described in the GeneScreen Plus protocol by the manufacturer. Resulting signal blots were compared and normalized based on the N gene transcript band of the control lane (the mN $R_1$ plant producing a high level of the N gene transcript) included in each blot. The transgenic plants that gave density readings (Hewlet ScanJet™ and Image Analysis Program) between 100 and 150 were rated as high expressors, while the plants with densities between 15 and 50 were rated as low expressors.

Inoculation of transgenic plants with Tospovirus was carried out as described above with inoculation being done at the 3–4 leaf stage except where indicated.

Tobacco protoplasts were prepared from surface-sterilized leaves derived from $R_1$ plants [see Z. Pflanzanphysiol. 78:453 (1992) with modifications]. The isolated protoplasts ($6\times10^6$ protoplasts) were transformed with 0.68 $OD_{260\ nm}$ of the purified TSWV-BL virion preparation using the PEG method [see Plant Mol. Biol. 8:363 (1987)]. The transformed protoplasts were then cultured at the final density of $1\times10^6$ protoplasts/ml in the culture medium at 26° C. in the dark. After various intervals of incubation, the cultured protoplasts were washed twice with W5 solution and lysed by osmotic shock in the enzyme conjugate buffer. Viral multiplication (replication) was estimated by measuring the N protein of the virus using DAS-ELISA.

As described, one aspect of the present invention demonstrated that transgenic tobacco producing none or barely detectable amounts of the N protein were resistant to homologous and closely related isolates. This result suggested that the observed resistance may have been due to trans interactions of the incoming viral N gene RNA with either the N gene transcript produced in the transgenic plants or the N coding sequence itself. To test whether the presence of the nuclear N gene plays a role, transgenic P°N $R_0$ lines and $R_1$ plants from two P°N lines were challenged with four Tospoviruses (TSWV-BL, TSWV-10W, INSV-Beg and TSWV-B). Only asymptomatic plants were rated resistant while plants showing any symptoms were rated susceptible. All inoculated $R_0$ and $R_1$ plants were susceptible to the viruses.

To further test the possibility that the transcript of the N transgene is involved in the protection, a number of $R_0$ transgenic plants that produced either the sense or the antisense N gene transcript but not the N protein were inoculated with the homologous isolate. Results appear in the following table:

| Form of transgene[a] | Level of N gene RNA[b] | No. of R0 lines tested | No. of lines inoculated[c] | No. of lines resistant |
|---|---|---|---|---|
| mN | H | 8 | 4 | 0 |
| | L | 17 | 16 | 16 |
| | nd | 4 | 1 | 0 |
| asN | H | 6 | 3 | 0 |
| | L | 9 | 5 | 5 |
| | nd | 1 | 0 | 0 |
| P°N | nd | 12 | 6 | 0 |

[a]mN and asN represent plants expressing the sense and antisense untranslatable N genes, respectively, P°N represents plants containing the promotorless N gene;
[b]the level of the N gene RNA was estimated in each line by Northern blots, nd indicates that the N gene transcript was not detected;
[c]30-fold diluted leaf extracts of the *N. benthamiana* plants infected with TSWV-BL were applied to three leaves of each plant at the 6–7 leaf stage. Each extract was first applied to all test plants followed by control healthy plants. Data were taken daily for 45 days after inoculation and only the asymptomatic plants were rated resistant.

Unlike the controls, which developed typical systemic symptoms 7 to 9 days after inoculation, 16 out of 21 mN plants and 5 our of 8 asN plants were asymptomatic throughout their life cycles. Northern blot analysis of leaf tissues sampled before inoculation showed that all the resistant $R_0$ lines produced low levels of the sense or antisense N gene RNA, whereas the susceptible $R_0$ lines produced either none or high levels of the RNA species. Since this data suggested that the resistance of transgenic plants to TSWV-BL was related to their relative levels of N gene transcript, transgenic progenies from four mN and three asN $R_0$ lines with either high or low N gene transcript levels were selected by germination on kanamycin-containing media. These transgenic plants were tested for resistance to the four Tospoviruses at the 3 to 4 leaf stage, except that some $R_1$ plants from two asN lines were inoculated at the 6 to 7 leaf stage. The results are summarized in the following table:

| $R_0$ Line | N gene RNA[a] | TSWV-BL | TSWV-10W | INSV-Beg | TSWV-B |
|---|---|---|---|---|---|
| Promoterless N gene | | | | | |
| P°N-1 | nd | 10/10 | 10/10 | 10/10 | 10/10 |
| P°N-2 | nd | 15/15 | 10/10 | 10/10 | 10/10 |
| N°-3 | nd | 8/8 | 6/6 | 6/6 | 6/6 |
| Untranslatable N gene | | | | | |
| mN-2 | H | 20/20 | 20/20 | 20/20 | 20/20 |
| mN-7 | H | 20/20 | 20/20 | 20/20 | 20/20 |
| mN-13 | L | 2/20 | 4/20 | 20/20 | 20/20 |
| mN-18 | L | 4/20 | 1/20 | 20/20 | 20/20 |
| N°-3 | nd | 24/24 | 32/32 | 24/24 | 24/24 |
| Antisense N gene | | | | | |
| asN-1 | L | <u>20/20</u>[b] | <u>20/20</u> | 20/20 | 20/20 |
| asN-4 | H | 20/20 (16/16)[c] | 20/20 (16/16) | 20/20 | 20/20 |
| asN-9 | L | <u>19/20</u> (3/41) | <u>20/20</u> (5/21) | 20/20 | 20/20 |
| N°-3 | nd | 16/16 (32/32) | 16/16 (20/20) | 16/16 | 16/16 |

[a]Northern analysis of $R_0$ lines from which the $R_1$ plants were derived (see preceding table);
[b]the underlined fractions indicate that most of susceptible $R_1$ plants displayed a significant delay of symptom appearance;
[c]the fraction in parenthesis represents the inoculation data obtained from plants inoculated at the 6–7 leaf stage; the remaining data in this table were generated from plants inoculated at the 3–4 leaf stage; inoculated plants were observed daily for 45 days after inoculation.

All $R_1$ plants from high expressor lines mN-2 and mN-7 were susceptible to infections by all Tospoviruses tested, and these plants did not show a delay of symptom appearance as compared to controls. In contrast, high proportions of the $R_1$ plants from low expressor lines mN-13 and -18 were resistant to homologous (TSWV-BL) and closely related (TSWV-10W) isolates, but not resistant to infections by distantly related Tospoviruses (INSV-Beg and TSWV-B). The resistance of asN $R_1$ plants from low expressor $R_0$ lines were markedly influenced by the TSWV isolate used for inoculation. All but one of the small $R_1$ plants (3–4 leaf stage) from low expressor lines asN-1 and -9 became infected, although there was a delay of symptom appearance, when inoculated with the homologous TSWV-BL or closely related TSWV-10W isolates. In contrast, most of the large $R_1$ plants (6–7 leaf stage) from line asN-9 were resistant to both isolates. In comparison, control $R_1$ plants and $R_1$ plants from the high expressor line such as asN-4 displayed no resistance to either of the isolates regardless of the size of test plants. Antisense RNA-mediated protection was not effective against infection by the distantly related INSV-Beg and TSWV-B isolates.

Anlayses of data presented in the above two tables suggest that sense and antisense RNA-mediated protections are observed only in low expressors of the N gene. The R1 asN plants that produced high levels of the antisense N gene transcript were as susceptible as control plants. In contrast, the asN low expressors displayed a delay in symptom appearance when inoculated at the 3–4 leaf stage and showed increased levels of resistant when inoculated at the 6–7 leaf stage.

Inhibition of viral replication in tobacco protoplasts expressing the sense or antisense form of untranslatable N coding sequence was also noted. In this instance, whole virion preparations of TSWV-BL were used to transfect protoplasts isolated from transgenic lines to investigate the effect of sense or antisense N gene transcript on replication of the incoming virus. Viral replication was determined by measuring the level of the N protein of the incoming virus in transfected protoplasts, and it was found that protoplasts derived from plants (mN-7 and asN-4) that produced high levels of the respective RNA transcripts supported the replication of the virus, whereas protoplasts from mN low expressor (mN-18) did not. Protoplasts from as asN low expressor (asN-9) supported much lower levels of viral replication.

Accordingly, in this aspect of the present invention we have shown that transgenic plants expressing sense or antisense form of untranslatable N gene coding sequence are resistant to homologous (TSWV-BL) and closely related (TSWV-10W), but not to distantly related (INSV-Beg and TSWV-B) Tospoviruses. The following table provides a comparison of resistance to Tospoviruses between transgenic tobacco expressing various forms of the TSWV-BL N gene:

| Tospovirus | Homology to TSWV-BL N Gene[b] | Form of the Transgene[a] | | | |
|---|---|---|---|---|---|
| | | N | mN | asN | P°N |
| TSWV-BL | 100% | R | R | R[c] | S |
| TSWV-10W | 99% | R | R | R[c] | S |
| INSV-Beg | 60% | R[c] | S | S | S |
| TSWV-B | 78% | S | S | S | S |

[a]reactions of transgenic tobacco and *N. benthamiana* plants expresssing the intact N gene (N) of TSWV-BL to inoculation with the four Tospoviruses are included for comparisons with inoculation results of transgenic plants containing untranslatable (mN), antisense (asN), and promoterless (P°N) N coding sequences, R = resistant, S = susceptible;
[b]the nucleotide sequences are as reported in Phytopathology 82:1223 (1992) and Phytopathology 83:728 (1993)
[c]level of resistance may depend upon the concentration of inoculum.

These results confirm and extend the earlier aspects of the present invention for RNA-mediated protection with TSWV. Furthermore, the protection is observed in plants producing low rather than high levels of the N gene transcript, and although earlier studies reported herein indicate that tobacco plants which produced high levels of the TSWV-BL N protein displayed resistance to INSV-Beg, this additional data indicates that since resistance to INSV-Beg was not observed in transgenic plants expressing the sense or anisense form of the untranslatable of the N gene thus clearly indicating that protection against INSV-Beg is due to the presence of the N protein and not the N gene transcript. Thus, it appears that two different mechanisms are involved in protection transgenic plants against TSWV and INSV Tospoviruses according to the present invention. One mechanism involves the N gene transcript (RNA-mediated), and another involves the N protein (protein-medicated). In addition, the results of the protoplast experiments indicate that N gene RNA-mediated protection is achieved through a process that inhibits viral replication, and the data contained in the above tables suggest that protection against the distantly related INSV-Beg isolate is conferred by the N protein or TSWV-BI, and not by the gene transcript.

Finally, further studies were conducted to provide still another aspect of the present invention—that a portion of the Tospovirus nucleoprotein gene provide protection of transgenic plants against infection by the Tospovirus. It has already been demonstrated above that the N gene RNA protects against homologous and closely related TSWV isolates while the N protein protects against the homologous isolate and distantly related INSV isolates; that N gene RNA-mediated protection is effective in plants expressing low levels of the N gene whereas N protein-mediated protection requires high levels of N protein accumulation; and that the N gene RNA-mediated protection is achieved through inhibition of viral replication. Based upon this prior data, we next set out to determine whether a portion of the N gene might work against infection by the virus. We found, as discussed below, that transgenic plants expressing about one-half of the N gene sequence is resistant to the virus.

The following describes the cloning of one-half N gene fragments of TSWV-BL in order to demonstrate this final aspect of the present invention. The first and second halves of both the translatable and untranslatable N gene ere generated by reverse transcription and then PCR as described above. As depicted in FIG. 8, the nucleotide deletion or insertions at the 5'-terminals of the untranslatable half N gene fragments are indicated by the dash symbol; ATG codons are underlined and all possible termination codons immediately after the initiation codon of the untranslatable half N gene fragments are shown in bold.

The first half of the N gene was produced by RT-PCR using oligoprimers i (5'-TACAGTGGATCCATGGTTAAGGTAATCCATAGGCTTGAC) (SEQ ID NO. 25), which is complementary to the central region of the TSWV-BL N gene, and ii (5'-AGCTAACCATGGTTAAGCTCACTAAGGAAAGCATTGTTGC) (SEQ ID NO. 26) for the translatable or iii (5'-AGCTAATCTAGAACCATGGATGACTCACTAAGGAAAGCATTGTTGC) (SEQ ID NO. 27) for the untranslatable first half N gene fragment, the latter two oligomer primers are identical to the 5'-terminus of the N gene. Similarly, the second half of the N gene was produced by RT-PCR using oligomer primers iv (5'-AGCATTGGATCCATGGTTAACACACTAAGCAAGCAC) (SEQ ID NO. 28) which is complementary to the 3'-noncoding region of the TSWV-BL N gene, and v (5'-TACAGTTCTAGAACCATGGATGATGCAAAGTCTGTGAGG) (SEQ ID NO. 29) for the translatable of vi (5'-AGATTCTCTAGACCATGGTGACTTGATGAGCAAAGTCTGTGAGGCTTGC) (SEQ ID NO. 30) for the untranslatable second half N gene fragment, the latter two oligomer primers are identical to the central region of the N gene. The oligomer primer iii contains a frameshift mutation immediately after the translation codon and several termination codons to block possible translation readthroughs while the oligomer primer vi contains several inframe termination codons immediately after the translation initiation codon.

The half gene fragments were purified on a 1.2% agarose gel as described above, and the gel-isolated gene fragments were digested with the restriction enzyme NcoI and directly cloned into NcoI-digested plant expression vector pBI525. The resulting plasmids were identified and designated as (1) pBI525-N containing the first half translatable N gene, (2) pBI525-1N' containing the first half untranslatable N gene, (3) pBI525-1N⁻ containing the first half translatable N gene in the antisense orientation, (4) pBI525-2N containing the second half trnaslatable N gene, (5) pBI525-2n' containing the second half untranslatable N gene, and (6) pBI525-2N⁻ containing the second half translatable N gene in the antisense orientation. The expression cassettes were then excised from plasmid pBI525 by digestion with HindIII/EcoRI and ligated as described above into the plant transformation vector pBIN19 that had been cut with the same enzymes. The resulting vectors as well as plasmid pBIN19 were transferred to *A. tumefaciens* strain LBA4404, using the procedure described by Holsters supra. Leaf discs of *N. benthamiana* were inoculated with *A. tumefaciens* strain LBA4404 containing the various constructs. Transgenic plants were self-pollinated and seeds were selectively germinated on kanamycin as described above.

Analysis of transgenic plants by PCR and Northern hybridization PCR was performed on each $R_0$ transgenic line as described previously. The oligomer primers i to vi were used to determine the presence of the N coding sequence of TSWV-BL. The oligomer primer 35S-Promoter (see Example VIII) was combined with one of the above oligomer primers to confirm the orientation (relative to the CaMV 35S promoter) of the half gene sequences inserted into the plant genome. Northern analysis was conducted as described in Example VIII.

Lettuce isolate of TSWV (TSWV-BL) was used to challenge transgenic plants. Inoculation was done using test plants at the 3–4 leaf stage as described above. To avoid the possibility of escapes, control pants were used in each experiment and each inoculum extract was used to first inoculate the transgenic plants followed by control plants.

The various constructs used in this aspect of the present invention are illustrated in FIG. 8. Translatable and untranslatable half N gene fragments were synthesized by RT-PCR and then cloned directly into the plant expression vector pBI525. The oligomer primers iii and iv, used for generation of untranslatable half N gene fragments by RT-PCR, contains a mutation immediately after the translation initiation codon and the resulting reading frame contains several termination codons to block possible translation readthroughs. Thus, both first and second half untranslatable N gene fragments should be incapable of producing the truncated N protein fragments when introduced into plants. Both translatable and untranslatable half N gene fragments were then placed downstream of the CaMV 35S promoter of the vector pBI525 in the sense orientation or in the antisense orientation. The expression of the half N coding sequences of TSWV-BL was thus controlled by a double CaMV 35S promoter fused to the 5'-untranslated leader sequence of alfalfa mosaic virus (ALMV) of the expression vector pBI525. Expression vectors that utilize the stacked double CaMV 35S promoter elements are known to yield higher levels of mRNA transcription than similar vectors with a single 35S promoter element. Expression cassettes were transferred from the vector pBI525 to the plant transformation vector pBIN19. The resulting plasmids as well as the control plasmid pBIN19 were then transferred into *A. tumefaciens* strain LBA4404. Transgenic plants were obtained with nomenclature of the transgenic lines shown in FIG. 8.

All the kanamycin-resistant transgenic lines were confirmed by PCR to contain the proper N coding sequences in the expected orientations. Each transgenic R0 line which was grown for seeds was then assayed using Northern blot. Six out of six 1N, four out of six 1N', six out of six 1N⁻, six out of six 2N, seven out of eight 2N', and six out of seven 2N⁻ transgenic $R_0$ lines were found to produce half N gene RNAs.

A set of transgenic $R_0$ plants were challenged with the homologous isolate TSWV-BL. Only asymptomatic plants were rated resistant while the plants showing any symptom (local lesions or systemic infections) were rated susceptible. All the inoculated $R_0$ control plants were susceptible to the virus; in contrast, two out of nine 1N', two out of six 1N⁻, four out of ten 2N', and one out of eight 2N⁻ $R_0$ lines were found to be completely resistant to the virus infection. Although none of the 1N and 2N $R_0$ lines showed high levels of resistance, some of those plants displayed significant delays of symptom appearance.

Another set of transgenic $R_0$ lines was brought to maturity for seed production. Seedlings were germinated on kanamycin-containing medium and inoculated with TSWV-BL. As shown in the following table, control seedlings and seedlings from some of the transgenic lines were susceptible to the isolate whereas seedlings from lines 1N-151, IN'-123, and 2N'-134 showed various levels of protection, ranging from delays in symptom expression to compete resistance.

| | No. plants infected/No. plants inoculated | | |
|---|---|---|---|
| $R_0$ line | 6 DPI | 15 DPI | 30 DPI |
| Control | 50/50 | | |
| 1N–149 | 17/17 | | |
| 1N–151 | 2/20 | 13/20 | 17/20 |
| 1N–123 | 16/20 | 17/20 | 17/20 |
| 1N–124 | 20/20 | | |
| 1N–126 | 19/19 | | |
| 1N+–130 | 12/15 | 15/15 | |
| 1N+–132 | 18/19 | 19/19 | |

-continued

| | No. plants infected/No. plants inoculated | | |
|---|---|---|---|
| R₀ line | 6 DPI | 15 DPI | 30 DPI |
| 2N-155 | 20/20 | | |
| 2N+-134 | 0/20 | 10/20 | 10/20 |
| 2N+-135 | 19/19 | | |
| 2N+-142 | 20/20 | | |
| 2N+-143 | 20/20 | | |

In the above table, 30-fold diluted extracts of infected *N. benthamiana* were used to inoculate transgenic plants at the 3–4 leaf stage followed by control transgenic plants. DPI 6 days post inoculation.

In summary, this aspect of the present invention shows that transgenic plants expressing the first or the second half of either translatable or untranslatable N gene fragment are highly resistant to the homologous TSWV-BL isolate. This result demonstrates that a portion of the N gene is sufficient for resistance to the virus.

A listing of all nucleotide and amino acid sequences described in the foregoing description of the present invention is as follows:

SEQUENCE LISTING

```
<160> NUMBER OF SEQ ID NOS: 35

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence:  probe

<400> SEQUENCE: 1
agcaggcaaa actcgcagaa cttgc                                            25

<210> SEQ ID NO 2
<211> LENGTH: 25
<212> TYPE: DNA
<213> ORGANISM: Tomato spotted wilt virus

<400> SEQUENCE: 2
gcaagttctg cgagttttgc ctgct                                            25

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence:  primer

<400> SEQUENCE: 3
agctaaccat ggttaagctc actaaggaaa gc                                    32

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence:  primer

<400> SEQUENCE: 4
agcattccat ggttaacaca ctaagcaagc ac                                    32

<210> SEQ ID NO 5
<211> LENGTH: 2216
<212> TYPE: DNA
<213> ORGANISM: Tomato spotted wilt virus

<400> SEQUENCE: 5
```

-continued

```
caagttgaaa gcaacaacag aactgtaaat tctcttgcag tgaaatctct gctcatgtca      60
gcagaaaaca acatcatgcc taactctcaa gcttccactg attctcattt caagctgagc     120
ctctggctaa gggttccaaa ggttttgaag caggtttcca ttcagaaatt gttcaaggtt     180
gcaggagatg aaacaaacaa aacattttat ttatctattg cctgcattcc aaaccataac     240
agtgttgaga cagctttaaa cattactgtt atttgcaagc atcagctccc aattcgcaaa     300
tgcaaagctc cttttgaatt atcaatgatg ttttctgatt taaaggagcc ttacaacatt     360
gttcatgacc cttcataccc caaggatcg gttccaatgc tctggctcga aactcacaca      420
tctttgcaca agttctttgc aactaacttg caagaagatg taatcatcta cacttttgaac    480
aaccttgagc taactcctgg aaagttagat ttaggtgaaa gaaccttgaa ttacagtgaa     540
gatgcctaca aaaggaaata tttcctttca aaaacacttg aatgtcttcc atctaacaca     600
caaactatgt cttacttaga cagcatccaa atcccttcat ggaagataga ctttgccaga     660
ggagaaatta aaatttctcc acaatctatt tcagttgcaa aatctttgtt aaagcttgat     720
ttaagcggga tcaaaaagaa agaatctaag gttaaggaag cgtatgcttc aggatcaaaa     780
taatcttgct ttgtccagct tttctaatt atgttatgtt tattttcttt ctttacttat      840
aattatttct ctgtttgtca tctctttcaa attcctcctg tctagtagaa accataaaaa     900
caaaaataa aaatgaaaat aaaattaaaa taaaataaaa tcaaaaaatg aaataaaaac      960
aacaaaaaat taaaaacga aaaccaaaa agacccgaaa gggaccaatt tggccaaatt      1020
tgggttttgt ttttgttttt tgtttttgt ttttttattt ttatttatt tttattttat      1080
tttatttta ttttatttt attttattta tttttttgtt tcgttgtttt tgttattttta     1140
ttatttatta agcacaacac acagaaagca aactttaatt aaacacactt atttaaaatt    1200
taacacacta agcaagcaca agcaataaag ataagaaag ctttatatat ttataggctt     1260
ttttataatt taactacag ctgctttcaa gcaagttctg cgagttttgc ctgcttttta     1320
accccgaaca tttcatagaa cttgttaaga gtttcactgt aatgttccat agcaacactc    1380
cctttagcat taggattgct ggagctaagt atagcagcat actctttccc cttcttcacc    1440
tgatcttcat tcatttcaaa tgctttgctt ttcagcacag tgcaaacttt tcctaaggct    1500
tccttggtgt catacttctt tgggtcgatc ccgaggtcct tgtatttgc atcctgatat     1560
atagccaaga caacactgat catctcaaag ctatcaactg aagcaataag aggtaagcta    1620
cctcccagca ttatggcaag tctcacagac tttgcatcat cgagaggtaa tccataggct    1680
tgaatcaaag gatgggaagc aatcttagat ttgatagtat tgagattctc agaattccca    1740
gtttcttcaa caagcctgac cctgatcaag ctatcaagcc ttctgaaggt catgtcagtg    1800
cctccaatcc tgtctgaagt tttctttatg gtaattttac caaaagtaaa atcgctttgc    1860
ttaataacct tcattatgct ctgacgattc tttaggaatg tcagacatga ataacgctc     1920
atcttcttga tctggtcgat gttttccaga caaaagtct tgaagttgaa tgctaccaga     1980
ttctgatctt cctcaaactc aaggtctttg ccttgtgtca acaaagcaac aatgctttcc    2040
ttagtgagct taaccttaga catgatgatc gtaaaagttg ttatatgctt tgaccgtatg    2100
taactcaagg tgcgaaagtg caactctgta tcccgcagtc gtttcttagg ttcttaatgt    2160
gatgatttgt aagactgagt gttaaggtat gaacacaaaa ttgacacgat tgctct        2216
```

<210> SEQ ID NO 6
<211> LENGTH: 1709
<212> TYPE: DNA
<213> ORGANISM: Tomato spotted wilt virus

```
<400> SEQUENCE: 6
aaattctctt gcagtgaaat ctctgctcat gttagcagaa acaacatca tgcctaactc      60 tcaagctttt gtcaaagctt ctactgattc taatttcaag ctgagcctct ggctaagggt     120
tccaaaggtt ttgaagcaga tttccattca gaaattgttc aaggttgcag agatgaaac     180 aaataaaaca ttttatttat ctattgcctg cattccaaac cataacagtg ttgagacagc     240
tttaaacatt actgttattt gcaagcatca gctcccaatt cgtaaatgta aaactccttt     300
tgaattatca atgatgttt ctgatttaaa ggagccttac aacattattc atgatccttc      360
atatccccaa aggattgttc atgctctgct tgaaactcac acatcttttg cacaagttct     420
ttgcaacaac ttgcaagaag atgtgatcat ctacaccttg aacaaccatg agctaactcc     480
tggaaagtta gatttaggtg aaataacttt gaattacaat gaagacgcct acaaaaggaa     540
atatttcctt tcaaaaacac ttgaatgtct tccatctaac atacaaacta tgtcttattt     600
agacagcatc caaatcccctt cctggaagat agactttgcc aggggagaaa ttaaaatttc     660
tccacaatct atttcagttg caaaatcttt gttaaatctt gatttaagcg ggattaaaaa     720
gaaagaatct aagattaagg aagcatatgc ttcaggatca aaatgatctt gctgtgtcca     780 gcttttcta attatgttat gtttatttc tttcttact tataattatt tttctgtttg       840
tcatttcttt caaattcctc ctgtctagta gaaaccataa aaacaaaaat aaaaataaaa     900
taaaatcaaa ataaaataaa atcaaaaaa tgaaataaaa gcaacaaaaa aattaaaaaa     960
caaaaaacca aaaagatcc cgaaaggaca attttggcca aatttggggt ttgttttgt     1020 tttttgtttt tttgtttttt gtttttattt ttatttttat ttttattttt attttatttt     1080
attttatgtt tttgttgttt ttgttatttt gttatttatt aagcacaaca cacagaaagc     1140
aaactttaat taaacacact tatttaaaat ttaacacact aagcaagcac aaacaataaa     1200
gataaagaaa gctttatata tttataggct ttttttataat ttaacttaca gctgcttta     1260 agcaagttct gtgagttttg cctgtttttt aaccccaaac atttcataga acttgttaag     1320
ggtttcactg taatgttcca tagcaatact tcctttagca ttaggattgc tggagctaag     1380
tatagcagca tactctttcc ccttcttcac ctgatcttca ttcatttcaa atgcttttct     1440
tttcagcaca gtgcaaactt ttcctaaggc ttccctggtg tcatacttct ttgggtcgat     1500
cccgagatcc ttgtattttg catcctgata tatagccaag acaacactga tcatctcaaa     1560
gctatcaact gaagcaataa gaggtaagct acctcccagc attatggcaa gcctcacaga     1620
ctttgcatca tcaagaggta atccataggc ttgaatcaaa gggtgggaag caatcttaga     1680
tttgatagta ttgagattct cagaattcc                                       1709

<210> SEQ ID NO 7
<211> LENGTH: 260
<212> TYPE: PRT
<213> ORGANISM: Tomato spotted wilt virus

<400> SEQUENCE: 7

Gln Val Glu Ser Asn Asn Arg Thr Val Asn Ser Leu Ala Val Lys Ser
 1               5                  10                  15

Leu Leu Met Ser Ala Glu Asn Asn Ile Met Pro Asn Ser Gln Ala Ser
            20                  25                  30

Thr Asp Ser His Phe Lys Leu Ser Leu Trp Leu Arg Val Pro Lys Val
        35                  40                  45

Leu Lys Gln Val Ser Ile Gln Lys Leu Phe Lys Val Ala Gly Asp Glu
```

|            |     |     |     |     |     |     |     |     |     |     |     |     |     |     |     |
|------------|-----|-----|-----|-----|-----|-----|-----|-----|-----|-----|-----|-----|-----|-----|-----|
|            |     |     |     | 50  |     |     |     | 55  |     |     |     | 60  |     |     |     |
| Thr | Asn | Lys | Thr | Phe | Tyr | Leu | Ser | Ile | Ala | Cys | Ile | Pro | Asn | His | Asn |
| 65  |     |     |     |     | 70  |     |     |     |     | 75  |     |     |     |     | 80  |
| Ser | Val | Glu | Thr | Ala | Leu | Asn | Ile | Thr | Val | Ile | Cys | Lys | His | Gln | Leu |
|     |     |     |     | 85  |     |     |     |     | 90  |     |     |     |     | 95  |     |
| Pro | Ile | Arg | Lys | Cys | Lys | Ala | Pro | Phe | Glu | Leu | Ser | Met | Met | Phe | Ser |
|     |     |     | 100 |     |     |     |     | 105 |     |     |     |     | 110 |     |     |
| Asp | Leu | Lys | Glu | Pro | Tyr | Asn | Ile | Val | His | Asp | Pro | Ser | Tyr | Pro | Lys |
|     |     |     | 115 |     |     |     |     | 120 |     |     |     |     | 125 |     |     |
| Gly | Ser | Val | Pro | Met | Leu | Trp | Leu | Glu | Thr | His | Thr | Ser | Leu | His | Lys |
|     |     | 130 |     |     |     |     | 135 |     |     |     |     | 140 |     |     |     |
| Phe | Phe | Ala | Thr | Asn | Leu | Gln | Glu | Asp | Val | Ile | Ile | Tyr | Thr | Leu | Asn |
| 145 |     |     |     |     | 150 |     |     |     |     | 155 |     |     |     |     | 160 |
| Asn | Leu | Glu | Leu | Thr | Pro | Gly | Lys | Leu | Asp | Leu | Gly | Glu | Arg | Thr | Leu |
|     |     |     |     | 165 |     |     |     |     | 170 |     |     |     |     | 175 |     |
| Asn | Tyr | Ser | Glu | Asp | Ala | Tyr | Lys | Arg | Lys | Tyr | Phe | Leu | Ser | Lys | Thr |
|     |     |     | 180 |     |     |     |     | 185 |     |     |     |     | 190 |     |     |
| Leu | Glu | Cys | Leu | Pro | Ser | Asn | Thr | Gln | Thr | Met | Ser | Tyr | Leu | Asp | Ser |
|     |     | 195 |     |     |     |     | 200 |     |     |     |     | 205 |     |     |     |
| Ile | Gln | Ile | Pro | Ser | Trp | Lys | Ile | Asp | Phe | Ala | Arg | Gly | Glu | Ile | Lys |
|     | 210 |     |     |     |     | 215 |     |     |     |     | 220 |     |     |     |     |
| Ile | Ser | Pro | Gln | Ser | Ile | Ser | Val | Ala | Lys | Ser | Leu | Leu | Lys | Leu | Asp |
| 225 |     |     |     |     | 230 |     |     |     |     | 235 |     |     |     |     | 240 |
| Leu | Ser | Gly | Ile | Lys | Lys | Lys | Glu | Ser | Lys | Val | Lys | Glu | Ala | Tyr | Ala |
|     |     |     |     | 245 |     |     |     |     | 250 |     |     |     |     | 255 |     |
| Ser | Gly | Ser | Lys |     |     |     |     |     |     |     |     |     |     |     |     |
|     |     |     | 260 |     |     |     |     |     |     |     |     |     |     |     |     |

<210> SEQ ID NO 8
<211> LENGTH: 858
<212> TYPE: DNA
<213> ORGANISM: Tomato spotted wilt virus

<400> SEQUENCE: 8

```
ttaacacact aagcaagcac aaacaataaa gataaagaaa gctttatata tttataggct      60
tttttataat ttaacttaca gctgctttta agcaagttct gtgagttttg cctgtttttt     120
aaccccaaac atttcataga acttgttaag ggtttcactg taatgttcca tagcaatact     180
tcctttagca ttaggattgc tggagctaag tatagcagca tactctttcc ccttcttcac     240
ctgatcttca ttcatttcaa atgcttttct tttcagcaca gtgcaaactt ttcctaaggc     300
ttccctggtg tcatacttct ttgggtcgat cccgagatcc ttgtattttg catcctgata     360
tatagccaag acaacactga tcatctcaaa gctatcaact gaagcaataa gaggtaagct     420
acctcccagc attatggcaa gcctcacaga ctttgcatca tcaagaggta atccataggc     480
ttgactcaaa gggtgggaag caatcttaga tttgatagta ttgagattct cagaattccc     540
agtttcctca caagcctga  ccctgatcaa gctatcaagc cttctgaagg tcatgtcagt     600
ggctccaatc ctgtctgaag ttttctttat ggtaatttta ccaaaagtaa aatcgctttg     660
cttaataacc ttcattatgc tctgacgatt cttcaggaat gtcagacatg aaataatgct     720
catcttttg  atctggtcaa ggttttccag acaaaaagtc ttgaagttga atgctaccag     780
attctgatct tcctcaaact caaggtcttt gccttgtgtc aacaaagcaa caatgctttc     840
cttagtgagc ttaaccat                                                   858
```

<210> SEQ ID NO 9
<211> LENGTH: 2028
<212> TYPE: DNA
<213> ORGANISM: Tomato spotted wilt virus

<400> SEQUENCE: 9

| | | | | | |
|---|---|---|---|---|---|
| aaattctctt | gcagtgaaat | ctctgctcat | gttagcagaa | acaacatca | tgcctaactc | 60 |
| tcaagctttt | gtcaaagctt | ctactgattc | taatttcaag | ctgagcctct | ggctaagggt | 120 |
| tccaaaggtt | ttgaagcaga | tttccattca | gaaattgttc | aaggttgcag | gagatgaaac | 180 |
| aaataaaaca | ttttatttat | ctattgcctg | cattccaaac | cataacagtg | ttgagacagc | 240 |
| tttaaacatt | actgttattt | gcaagcatca | gctcccaatt | cgtaaatgta | aaactccttt | 300 |
| tgaattatca | atgatgtttt | ctgatttaaa | ggagccttac | aacattattc | atgatccttc | 360 |
| atatccccaa | aggattgttc | atgctctgct | tgaaactcac | acatcttttg | cacaagttct | 420 |
| ttgcaacaac | ttgcaagaag | atgtgatcat | ctacaccttg | aacaaccatg | agctaactcc | 480 |
| tggaaagtta | gatttaggtg | aaataacttt | gaattacaat | gaagacgcct | acaaaaggaa | 540 |
| atatttcctt | tcaaaaacac | ttgaatgtct | tccatctaac | atacaaacta | tgtcttattt | 600 |
| agacagcatc | caaatcccctt | cctggaagat | agactttgcc | agggggagaaa | ttaaaatttc | 660 |
| tccacaatct | atttcagttg | caaaatcttt | gttaaatctt | gatttaagcg | ggattaaaaa | 720 |
| gaaagaatct | aagattaagg | aagcatatgc | ttcaggatca | aaatgatctt | gctgtgtcca | 780 |
| gcttttctta | attatgttat | gtttatttc | tttctttact | tataattatt | tttctgtttg | 840 |
| tcatttcttt | caaattcctc | ctgtctagta | gaaaccataa | aacaaaaat | aaaaataaaa | 900 |
| taaaatcaaa | ataaaataaa | aatcaaaaaa | tgaaataaaa | gcaacaaaaa | aattaaaaaa | 960 |
| caaaaaacca | aaaaagatcc | cgaaaggaca | attttggcca | aatttggggt | ttgttttgt | 1020 |
| tttttgtttt | tttgtttttt | gttttttattt | ttatttttat | ttttattttt | attttattttt | 1080 |
| atttttatgtt | tttgttgttt | tgttatttt | gttatttatt | aagcacaaca | cacagaaagc | 1140 |
| aaactttaat | taaacacact | tatttaaaat | ttaacacact | aagcaagcac | aaacaataaa | 1200 |
| gataaagaaa | gctttatata | tttataggct | ttttttataat | ttaacttaca | gctgctttta | 1260 |
| agcaagttct | gtgagttttg | cctgtttttt | aacccccaaac | atttcataga | acttgttaag | 1320 |
| ggtttcactg | taatgttcca | tagcaatact | tcctttagca | ttaggattgc | tggagctaag | 1380 |
| tatagcagca | tactctttcc | ccttcttcac | ctgatcttca | ttcatttcaa | atgcttttct | 1440 |
| tttcagcaca | gtgcaaactt | ttcctaaggc | ttccctggtg | tcatacttct | ttgggtcgat | 1500 |
| cccgagatcc | ttgtatttg | catcctgata | tatagccaag | acaacactga | tcatctcaaa | 1560 |
| gctatcaact | gaagcaataa | gaggtaagct | acctcccagc | attatggcaa | gcctcacaga | 1620 |
| ctttgcatca | tcaagaggta | atccataggc | ttgactcaaa | gggtgggaag | caatcttaga | 1680 |
| tttgatagta | ttgagattct | cagaattccc | agtttcctca | acaagcctga | ccctgatcaa | 1740 |
| gctatcaagc | cttctgaagg | tcatgtcagt | ggctccaatc | ctgtctgaag | ttttctttat | 1800 |
| ggtaatttta | ccaaaagtaa | aatcgctttg | cttaataacc | ttcattatgc | tctgacgatt | 1860 |
| cttcaggaat | gtcagacatg | aaataatgct | catctttttg | atctggtcaa | ggttttccag | 1920 |
| acaaaagtc | ttgaagttga | atgctaccag | attctgatct | tcctcaaact | caaggtcttt | 1980 |
| gccttgtgtc | aacaaagcaa | caatgctttc | cttagtgagc | ttaaccat | | 2028 |

<210> SEQ ID NO 10
<211> LENGTH: 21

```
<212> TYPE: DNA
<213> ORGANISM: Artificial Sequence
<220> FEATURE:
<223> OTHER INFORMATION: Description of Artificial Sequence: primer

<400> SEQUENCE: 10
ttctggtctt cttcaaactc a                                              21

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 11
ctgtagccat gagcaaag                                                  18

<210> SEQ ID NO 12
<211> LENGTH: 467
<212> TYPE: PRT
<213> ORGANISM: Tomato spotted wilt virus

<400> SEQUENCE: 12
```

Met Ser Ser Gly Val Tyr Glu Ser Ile Ile Gln Thr Lys Ala Ser Val
 1               5                  10                  15

Trp Gly Ser Thr Ala Ser Gly Lys Ser Ile Val Asp Ser Tyr Trp Ile
                20                  25                  30

Tyr Glu Phe Pro Thr Gly Ser Pro Leu Val Gln Thr Gln Leu Tyr Ser
            35                  40                  45

Asp Ser Arg Ser Lys Ser Ser Phe Gly Tyr Thr Ser Lys Ile Gly Asp
        50                  55                  60

Ile Pro Ala Val Glu Glu Ile Leu Ser Gln Asn Val His Ile Pro
 65                  70                  75                  80

Val Phe Asp Asp Ile Asp Phe Ser Ile Asn Ile Asn Asp Ser Phe Leu
                85                  90                  95

Ala Ile Ser Val Cys Ser Asn Thr Val Asn Thr Asn Gly Val Lys His
            100                 105                 110

Gln Gly His Leu Lys Val Leu Ser Leu Ala Gln Leu His Pro Phe Glu
        115                 120                 125

Pro Val Met Ser Arg Ser Glu Ile Ala Ser Arg Phe Arg Leu Gln Glu
130                 135                 140

Glu Asp Ile Ile Pro Asp Asp Lys Tyr Ile Ser Ala Ala Asn Lys Gly
145                 150                 155                 160

Ser Leu Ser Cys Val Lys Glu His Thr Tyr Lys Val Glu Met Ser His
                165                 170                 175

Asn Gln Ala Leu Gly Lys Val Asn Val Leu Ser Pro Asn Arg Asn Val
            180                 185                 190

His Glu Trp Leu Tyr Ser Phe Lys Pro Asn Phe Asn Gln Ile Glu Ser
        195                 200                 205

Asn Asn Arg Thr Val Asn Ser Leu Ala Val Lys Ser Leu Leu Met Ala
    210                 215                 220

Thr Glu Asn Asn Ile Met Pro Asn Ser Gln Ala Phe Val Lys Ala Ser
225                 230                 235                 240

Thr Asp Ser His Phe Lys Leu Ser Leu Trp Leu Arg Ile Pro Lys Val
                245                 250                 255

Leu Lys Gln Ile Ala Ile Gln Lys Leu Phe Lys Phe Ala Gly Asp Glu
            260                 265                 270

-continued

```
Thr Gly Lys Ser Phe Tyr Leu Ser Ile Ala Cys Ile Pro Asn His Asn
            275                 280                 285

Ser Val Glu Thr Ala Leu Asn Val Thr Val Ile Cys Arg His Gln Leu
        290                 295                 300

Pro Ile Pro Lys Ser Lys Ala Pro Phe Glu Leu Ser Met Ile Phe Ser
305                 310                 315                 320

Asp Leu Lys Glu Pro Tyr Asn Thr Val His Asp Pro Ser Tyr Pro Gln
                325                 330                 335

Arg Ile Val His Ala Leu Leu Glu Thr His Thr Ser Phe Ala Gln Val
            340                 345                 350

Leu Cys Asn Lys Leu Gln Glu Asp Val Ile Ile Tyr Thr Ile Asn Ser
        355                 360                 365

Pro Glu Leu Thr Pro Ala Lys Leu Asp Leu Gly Glu Arg Thr Leu Asn
370                 375                 380

Tyr Ser Glu Asp Ala Ser Lys Lys Lys Tyr Phe Leu Ser Lys Thr Leu
385                 390                 395                 400

Glu Cys Leu Pro Val Asn Val Gln Thr Met Ser Tyr Leu Asp Ser Ile
                405                 410                 415

Gln Ile Pro Ser Trp Lys Ile Asp Phe Ala Arg Gly Glu Ile Arg Ile
            420                 425                 430

Ser Pro Gln Ser Thr Pro Ile Ala Arg Ser Leu Leu Lys Leu Asp Leu
        435                 440                 445

Ser Lys Ile Lys Glu Lys Lys Ser Leu Thr Trp Glu Thr Ser Ser Tyr
450                 455                 460

Asp Leu Glu
465
```

<210> SEQ ID NO 13
<211> LENGTH: 258
<212> TYPE: PRT
<213> ORGANISM: Tomato Spotted Wilt Virus (Brazil isolate)

<400> SEQUENCE: 13

```
Met Ser Lys Val Lys Leu Thr Lys Glu Asn Ile Val Ser Leu Leu Thr
  1               5                  10                  15

Gln Ser Ala Asp Val Glu Phe Glu Glu Asp Gln Asn Gln Val Ala Phe
             20                  25                  30

Asn Phe Lys Thr Phe Cys Gln Glu Asn Leu Asp Leu Ile Lys Lys Met
         35                  40                  45

Ser Ile Thr Ser Cys Leu Thr Phe Leu Lys Asn Arg Gln Gly Ile Met
     50                  55                  60

Lys Val Val Asn Gln Ser Asp Phe Thr Phe Gly Lys Val Thr Ile Lys
 65                  70                  75                  80

Lys Asn Ser Glu Arg Val Gly Ala Lys Asp Met Thr Phe Arg Arg Leu
                 85                  90                  95

Asp Ser Met Ile Arg Val Lys Leu Ile Glu Glu Thr Ala Asn Asn Glu
            100                 105                 110

Asn Leu Ala Ile Ile Lys Ala Lys Ile Ala Ser His Pro Leu Val Gln
        115                 120                 125

Ala Tyr Gly Leu Pro Leu Ala Asp Ala Lys Ser Val Arg Leu Ala Ile
    130                 135                 140

Met Leu Gly Gly Ser Ile Pro Leu Ile Ala Ser Val Asp Ser Phe Glu
145                 150                 155                 160

Met Ile Ser Val Val Leu Ala Ile Tyr Gln Asp Ala Lys Tyr Lys Glu
```

-continued

```
            165                 170                 175
Leu Gly Ile Glu Pro Thr Lys Tyr Asn Thr Lys Glu Ala Leu Gly Lys
                180                 185                 190

Val Cys Thr Val Leu Lys Ser Lys Gly Phe Thr Met Asp Asp Ala Gln
            195                 200                 205

Ile Asn Lys Gly Lys Glu Tyr Ala Lys Ile Leu Ser Ser Cys Asn Pro
        210                 215                 220

Asn Ala Lys Gly Ser Ile Ala Met Asp Tyr Tyr Ser Asp Asn Leu Asp
225                 230                 235                 240

Lys Phe Tyr Glu Met Phe Gly Val Lys Lys Glu Ala Lys Ile Ala Gly
                245                 250                 255

Val Ala
```

<210> SEQ ID NO 14
<211> LENGTH: 3049
<212> TYPE: DNA
<213> ORGANISM: Tomato Spotted Wilt Virus (Brazil isolate)

<400> SEQUENCE: 14

| | | | | | |
|---|---|---|---|---|---|
| agagcaattg | ggtcattttt | tattctaaat | cgaacctcaa | ctagcaaatc | tcagaactgt | 60 |
| aataagcaca | agagcacaag | agccacaatg | tcatcaggtg | tttatgaatc | gatcattcag | 120 |
| acaaaggctt | cagtttgggg | atcgacagca | tctggtaagt | ccatcgtgga | ttcttactgg | 180 |
| atttatgagt | ttccaactgg | ttctccactg | gttcaaactc | agttgtactc | tgattcgagg | 240 |
| agcaaaagta | gcttcggcta | cacttcaaaa | attggtgata | ttcctgctgt | agaggaggaa | 300 |
| atttatctc | agaacgttca | tatcccagtg | tttgatgata | ttgatttcag | catcaatatc | 360 |
| aatgattctt | tcttggcaat | ttctgttgt | tccaacacag | ttaacaccaa | tggagtgaag | 420 |
| catcagggtc | atcttaaagt | tctttctctt | gcccaattgc | atcctttga | acctgtgatg | 480 |
| agcaggtcag | agattgctag | cagattccgg | ctccaagaag | aagatataat | tcctgatgac | 540 |
| aaatatatat | ctgctgctaa | caagggatct | ctctcctgtg | tcaaagaaca | tacttacaaa | 600 |
| gtcgaaatga | gccacaatca | ggctttaggc | aaagtgaatg | ttctttctcc | taacagaaat | 660 |
| gttcatgagt | ggctgtatag | tttcaaacca | aatttcaacc | agatcgaaag | taataacaga | 720 |
| actgtaaatt | ctccttgcagt | caaatctttg | ctcatggcta | cagaaaacaa | cattatgcct | 780 |
| aactctcaag | cttttgttaa | agcttctact | gattctcatt | ttaagttgag | cctttggctg | 840 |
| agaattccaa | aagttttgaa | gcaaatagcc | atacagaagc | tcttcaagtt | tgcaggagac | 900 |
| gaaaccggta | aagtttcta | tttgtctatt | gcatgcatcc | caaatcacaa | cagtgtggaa | 960 |
| acagctttaa | atgtcactgt | tatatgtaga | catcagcttc | caatccctaa | gtccaaagct | 1020 |
| ccttttgaat | tatcaatgat | tttctccgat | ctgaaagagc | cttacaacac | tgtgcatgat | 1080 |
| ccttcatatc | ctcaaaggat | tgttcatgct | ttgcttgaga | ctcacacttc | ctttgcacaa | 1140 |
| gttctctgca | acaagctgca | agaagatgtg | atcatatata | ctataaacag | ccctgaacta | 1200 |
| accccagcta | agctggatct | aggtgaaaga | accttgaact | acagtgaaga | tgcttcgaag | 1260 |
| aagaagtatt | ttctttcaaa | aacactcgaa | tgcttgccag | taaatgtgca | gactatgtct | 1320 |
| tatttggata | gcatccagat | tccttcatgg | aagatagact | ttgccagagg | agagatcaga | 1380 |
| atctccctc | aatctactcc | tattgcaaga | tctttgctca | agctggattt | gagcaagatc | 1440 |
| aaggaaaaga | agtccttgac | ttgggaaaca | tccagctatg | atctagaata | aaagtggctc | 1500 |
| atactactct | aagtagtatt | tgtcaacttg | cttatccttt | atgttgttta | tttcttttaa | 1560 |

-continued

```
atctaaagta agttagattc aagtagttta gtatgctata gcattattac aaaaaataca    1620
aaaaaataca aaaaatataa aaaacccaaa aagatcccaa aagggacgat                1680
ttggttgatt tactctgttt taggcttatc taagctgctt ttgtttgagc aaaataacat    1740
tgtaacatgc aataactgga atttaaagtc ctaaaagaag tttcaaagga cagcttagcc    1800
aaaattggtt tttgttttg tttttttgtt tttgttttt ttgttttatt tttatttta      1860
gtttattttt tgttttgtt attttattt ttattttatt ttcttttatt ttatttatat    1920
atatatcaaa cacaatccac acaaataatt ttaatttcaa acattctact gatttaacac    1980
acttagcctg actttatcac acttaacacg cttagttagg ctttaacaca ctgaactgaa    2040
ttaaaacaca cttagtatta tgcatctctt aattaacaca ctttaataat atgcatctct    2100
gaatcagcct taaagaagct tttatgcaac accagcaatc ttggcctctt tcttaactcc    2160
aaacatttca tagaatttgt caagattatc actgtaatag tccatagcaa tgcttcccctt   2220
agcattggga ttgcaagaac taagtatctt ggcatattct ttccctttgt ttatctgtgc    2280
atcatccatt gtaaatcctt tgcttttaag cactgtgcaa accttcccca gagcttcctt    2340
agtgttgtac ttagttggtt caatccctaa ctccttgtac tttgcatctt gatatatggc    2400
aagaacaaca ctgatcatct cgaagctgtc aacagaagca atgagaggga tactacctcc    2460
aagcattata gcaagtctca cagattttgc atctgccaga ggcagcccgt aagcttggac    2520
caaagggtgg gaggcaattt ttgctttgat aatagcaaga ttctcattgt ttgcagtctc    2580
ttctatgagc ttcactctta tcatgctatc aagcctcctg aaagtcatat ccttagctcc    2640
aactctttca gaattttttct ttatcgtgac cttaccaaaa gtaaaatcac tttggttcac    2700
aactttcata atgccttggc gattcttcaa gaaagtcaaa catgaagtga tactcatttt    2760
cttaatcagg tcaagatttt cctgacagaa agtcttaaag ttgaatgcga cctggttctg    2820
gtcttcttca aactcaacat ctgcagattg agttaaaaga gagacaatgt tttcttttgt    2880
gagcttgacc ttagacatgg tggcagttta gatctagacc tttctcgaga gataagattc    2940
aaggtgagaa agtgcaacac tgtagaccgc ggtcgttact tatcctgtta atgtgatgat    3000
ttgtattgct gagtattagg ttttttgaata aaattgacac aattgctct                3049
```

<210> SEQ ID NO 15
<211> LENGTH: 777
<212> TYPE: DNA
<213> ORGANISM: Tomato Spotted Wilt Virus (Brazil isolate)

<400> SEQUENCE: 15

```
ttatgcaaca ccagcaatct tggcctcttt cttaactcca aacatttcat agaatttgtc     60
aagattatca ctgtaatagt ccatagcaat gcttccctta gcattgggat tgcaagaact    120
aagtatcttg gcatattctt tccctttgtt tatctgtgca tcatccattg taaatccttt    180
gcttttaagc actgtgcaaa ccttccccag cttccttgtg ttgtact tagttggttc    240
aatccctaac tccttgtact ttgcatcttg atatatggca agaacaacac tgatcatctc    300
gaagctgtca acagaagcaa tgagagggat actacctcca agcattatag caagtctcac    360
agattttgca tctgccagag gcagcccgta agcttggacc aaagggtggg aggcaattt    420
tgctttgata atagcaagat tctcattgtt tgcagtctct tctatgagct tcactcttat    480
catgctatca agcctcctga aagtcatatc cttagctcca actctttcag aatttttctt    540
tatcgtgacc ttaccaaaag taaaatcact ttggttcaca actttcataa tgccttggcg    600
attcttcaag aaagtcaaac atgaagtgat actcattttc ttaatcaggt caagattttc    660
```

-continued

```
ctgacagaaa gtcttaaagt tgaatgcgac ctggttctgg tcttcttcaa actcaacatc    720
tgcagattga gttaaaagag agacaatgtt ttcttttgtg agcttgacct tagacat       777
```

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 16

```
gttctgagat ttgctagt                                                  18
```

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 17

```
ttatatcttc ttcttgga                                                  18
```

<210> SEQ ID NO 18
<211> LENGTH: 1401
<212> TYPE: DNA
<213> ORGANISM: Tomato spotted wilt virus

<400> SEQUENCE: 18

```
atgtcatcag gtgtttatga atcgatcatt cagacaaagg cttcagtttg ggggatcgaca    60 gcatctggta agtccatcgt ggattcttac tggatttatg agtttccaac tggttctcca    120
ctggttcaaa ctcagttgta ctctgattcg aggagcaaaa gtagcttcgg ctacacttca    180
aaaattggtg atattcctgc tgtagaggag gaaattttat ctcagaacgt tcatatccca    240
gtgtttgatg atattgattt cagcatcaat atcaatgatt ctttcttggc aatttctgtt    300
tgttccaaca cagttaacac caatggagtg aagcatcagg gtcatcttaa agttctttct    360
cttgcccaat tgcatccctt tgaacctgtg atgagcaggt cagagattgc tagcagattc    420
cggctccaag aagaagatat aattcctgat gacaaatata tatctgctgc taacaaggga    480
tctctctcct gtgtcaaaga acatacttac aaagtcgaaa tgagccacaa tcaggcttta    540
ggcaaagtga atgttctttc tcctaacaga aatgttcatg agtggctgta tagtttcaaa    600
ccaaatttca accagatcga aagtaataac agaactgtaa attctcttgc agtcaaatct    660
ttgctcatgg ctacagaaaa caacattatg cctaactctc aagcttttgt taaagcttct    720
actgattctc attttaagtt gagcctttgg ctgagaattc caaaagtttt gaagcaaata    780
gccatacaga agctcttcaa gtttgcagga gacgaaaccg gtaaaagttt ctatttgtct    840
attgcatgca tcccaaatca caacagtgtg gaaacagctt taaatgtcac tgttatatgt    900
agacatcagc ttccaatccc taagtccaaa gctccttttg aattatcaat gattttctcc    960
gatctgaaag agccttacaa cactgtgcat gatccttcat atcctcaaag gattgttcat   1020
gctttgcttg agactcacac ttcctttgca caagttctct gcaacaagct gcaagaagat   1080
gtgatcatat atactataaa cagccctgaa ctaaccccag ctaagctgga tctaggtgaa   1140
agaaccttga actacagtga agatgcttcg aagaagaagt attttctttc aaaaacactc   1200
gaatgcttgc cagtaaatgt gcagactatg tcttatttgg atagcatcca gattccttca   1260
```

```
tggaagatag actttgccag aggagagatc agaatctccc ctcaatctac tcctattgca    1320
agatctttgc tcaagctgga tttgagcaag atcaaggaaa agaagtcctt gacttgggaa    1380
acatccagct atgatctaga a                                              1401

<210> SEQ ID NO 19
<211> LENGTH: 777
<212> TYPE: DNA
<213> ORGANISM: Tomato spotted wilt virus

<400> SEQUENCE: 19
atgtctaagg tcaagctcac aaaagaaaac attgtctctc ttttaactca atctgcagat      60
gttgagtttg aagaagacca gaaccaggtc gcattcaact ttaagacttt ctgtcaggaa     120
aatcttgacc tgattaagaa aatgagtatc acttcatgtt tgactttctt gaagaatcgc     180
caaggcatta tgaaagttgt gaaccaaagt gattttactt ttggtaaggt cacgataaag     240
aaaaattctg aaagagttgg agctaaggat atgactttca ggaggcttga tagcatgata     300
agagtgaagc tcatagaaga gactgcaaac aatgagaatc ttgctattat caaagcaaaa     360
attgcctccc acccttttggt ccaagcttac gggctgcctc tggcagatgc aaaatctgtg     420
agacttgcta taatgcttgg aggtagtatc cctctcattg cttctgttga cagcttcgag     480
atgatcagtg ttgttcttgc catatatcaa gatgcaaagt acaaggagtt agggattgaa     540
ccaactaagt acaacactaa ggaagctctg gggaaggttt gcacagtgct aaaagcaaa      600 ggatttacaa tggatgatgc acagataaac aaagggaaag aatatgccaa gatacttagt     660
tcttgcaatc ccaatgctaa gggaagcatt gctatggact attacagtga taatcttgac     720
aaattctatg aaatgtttgg agttaagaaa gaggccaaga ttgctggtgt tgcataa       777

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence:  primer

<400> SEQUENCE: 20
tacttatcta gaaccatgga caaagcaaag attaccaagg                            40

<210> SEQ ID NO 21
<211> LENGTH: 42
<212> TYPE: DNA
<213> ORGANISM: Artificial Sequence
<220> FEATURE:
<223> OTHER INFORMATION: Description of Artificial Sequence:  primer

<400> SEQUENCE: 21
tacagtggat ccatggttat ttcaaataat ttataaaagc ac                          42

<210> SEQ ID NO 22
<211> LENGTH: 36
<212> TYPE: DNA
<213> ORGANISM: Artificial Sequence
<220> FEATURE:
<223> OTHER INFORMATION: Description of Artificial Sequence:  primer

<400> SEQUENCE: 22
agcattggat ccatggttaa cacactaagc aagcac                                 36

<210> SEQ ID NO 23
<211> LENGTH: 46
```

```
<212> TYPE: DNA
<213> ORGANISM: Artificial Sequence
<220> FEATURE:
<223> OTHER INFORMATION: Description of Artificial Sequence: primer

<400> SEQUENCE: 23
agctaatcta gaaccatgga tgactcacta aggaaagcat tgttgc        46

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 24
cccactatcc ttcgcaagac cc                                  22

<210> SEQ ID NO 25
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 25
tacagtggat ccatggttaa ggtaatccat aggcttgac                39

<210> SEQ ID NO 26
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 26
agctaaccat ggttaagctc actaaggaaa gcattgttgc               40

<210> SEQ ID NO 27
<211> LENGTH: 46
<212> TYPE: DNA
<213> ORGANISM: Artificial Sequence
<220> FEATURE:
<223> OTHER INFORMATION: Description of Artificial Sequence: primer

<400> SEQUENCE: 27
agctaatcta gaaccatgga tgactcacta aggaaagcat tgttgc        46

<210> SEQ ID NO 28
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 28
agcattggat ccatggttaa cacactaagc aagcac                   36

<210> SEQ ID NO 29
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 29
```

-continued

```
tacagttcta gaaccatgga tgatgcaaag tctgtgagg                          39

<210> SEQ ID NO 30
<211> LENGTH: 49
<212> TYPE: DNA
<213> ORGANISM: Artificial Sequence
<220> FEATURE:
<223> OTHER INFORMATION: Description of Artificial Sequence:  primer

<400> SEQUENCE: 30
agattctcta gaccatggtg acttgatgag caaagtctgt gaggcttgc               49

<210> SEQ ID NO 31
<211> LENGTH: 42
<212> TYPE: DNA
<213> ORGANISM: Tomato spotted wilt virus

<400> SEQUENCE: 31
atggttaagc tcactaagga aagcattgtt gctttgttga ca                      42

<210> SEQ ID NO 32
<211> LENGTH: 41
<212> TYPE: DNA
<213> ORGANISM: Artificial Sequence
<220> FEATURE:
<223> OTHER INFORMATION: Description of Artificial Sequence:  5'
      terminal sequence of untranslatable, mutated nucleocapsid DNA

<400> SEQUENCE: 32
atggatgact cactaaggaa agcattgttg ctttgttgac a                       41

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence:  5'
      terminal sequence of untranslatable, mutated nucleocapsid DNA

<400> SEQUENCE: 33
atggatgact cactaaggaa agcattgttg ctttgtgaca                         40

<210> SEQ ID NO 34
<211> LENGTH: 36
<212> TYPE: DNA
<213> ORGANISM: Artificial Sequence
<220> FEATURE:
<223> OTHER INFORMATION: Description of Artificial Sequence:  5'
      terminal sequence of DNA encoding approximately the C-terminal
      half of the tomato spotted wilt virus nucleocapsid protein

<400> SEQUENCE: 34
atggatgatg caaagtctgt gaggcttgcc ataatg                             36

<210> SEQ ID NO 35
<211> LENGTH: 42
<212> TYPE: DNA
<213> ORGANISM: Artificial Sequence
<220> FEATURE:
<223> OTHER INFORMATION: Description of Artificial Sequence:  5'
      terminal sequence of untranslatable, mutated nucleocapsid DNA

<400> SEQUENCE: 35
atggtgactt gatgagcaaa gtctgtgagg cttgccataa tg                      42
```

Thus while we have illustrated and described the preferred embodiments of our invention, it is to be understood that this invention is capable of variation and modification, and we therefore do not wish to be limited to the precise terms set forth, but desire to avail ourselves of such changes and alterations which may be made for adapting the invention to various usages and conditions. Such variations and modifications, for example, would include the substitution of structurally similar nucleic acid sequences in which the difference between the sequence shown and the variation sequence is such that little if any advantages are available with the variation sequence, i.e. that the sequences produce substantially similar results as described above. Thus, changes in sequence by the substitution, deletion, insertion or addition of nucleotides (in the nucleotide sequences) or amino acids (in the peptide sequences) which do not substantially alter the function of those sequences specifically described above are deemed to be within the scope of the present invention. In addition, it is our invention that the present invention may be modified to join the N genes of various isolates that provide resistance or immunity to Tospovirus infection of plants according to the present invention into a single cassette, and to use this cassette as a transgene in order to provide broad resistance to the Tospoviruses, especially to TSWV-BL, TSWV-B, and INSV. Accordingly, such changes and alterations are properly intended to be within the full range of equivalents, and therefore within the purview of the following claims.

Having thus described our invention and the manner and a process of making and using it in such full, clear, concise and exact terms so as to enable any person skilled in the art to which it pertains, or with which it is most nearly connected, to make and use the same.

We claim:

1. A DNA construct comprising a DNA molecule and transcriptional and translational regulatory sequences operably linked to the DNA molecule, the DNA molecule being modified from a nucleotide sequence encoding a nucleocapsid protein of an L serogroup Tospovirus, said DNA molecule being capable of transcription to a nontranslatable messenger RNA that does not translate to said nucleocapsid protein wherein, when the DNA construct is transformed into a plant cell, the DNA molecule is transcribed into the nontranslatable messenger RNA which exists at low level density readings of 15–50 as measured using a scanner and image analysis program, and confers resistance to said plant cell against an L serogroup Tosporivus.

2. The DNA construct according to claim 1, wherein the L serogroup Tospovirus is selected from the group consisting of TSWV-10W and TSWV-BL.

3. A recombinant DNA expression system comprising an expression vector into which is inserted the DNA construct according to claim 1.

4. A plant cell transformed with the DNA construct according to claim 1.

5. A transgenic plant transformed with the DNA construct according to claim 1.

6. A method of treating a plant cell comprising:
   transforming a plant cell with the DNA construct according to claim 1 and
   transcribing the DNA molecule under conditions effective to maintain the messenger RNA in the plant cell at low level density readings of 15–50, as measured using a scanner and image analysis program, wherein the plant cell acquires resistance to an L serogroup Tospovirus.

7. The method according to claim 6 wherein the L serogroup Tospovirus is TSWV-10W or TSWV-BL.

* * * * *